(12) United States Patent
Ario et al.

(10) Patent No.: US 6,274,367 B1
(45) Date of Patent: *Aug. 14, 2001

(54) DNA CODING FOR MAMMALIAN L-ASPARAGINASE

(75) Inventors: Takeshi Ario; Madoka Taniai; Kakuji Torigoe; Masashi Kurimoto, all of Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/309,592

(22) Filed: May 11, 1999

Related U.S. Application Data

(63) Continuation of application No. 09/008,481, filed on Jan. 16, 1998, now Pat. No. 6,087,151, which is a continuation-in-part of application No. 08/598,369, filed on Feb. 8, 1996, now abandoned.

(30) Foreign Application Priority Data

Feb. 8, 1995 (JP) .................................................. 7-042564

(51) Int. Cl.[7] .............................. C12N 9/82; C07H 21/04

(52) U.S. Cl. ................. 435/229; 435/252.3; 435/252.33; 435/320.1; 536/23.2; 536/23.5

(58) Field of Search ................................ 435/229, 252.3, 435/252.33, 320.1; 536/23.2, 23.5

(56) References Cited

FOREIGN PATENT DOCUMENTS 4-320684 11/1992 (JP) .

OTHER PUBLICATIONS

"Modified asparaginase free form antigenic activity", Chemical Asbtracts, vol. 92, No. 9, 92:71908n, p. 274 (Mar. 3, 1980).

Muramatsu, Masami ed., "Laboratory Manual for Genetic Engineering", Maruzen Co., Ltd., Tokyo, Japan, pp. i–vii (1988).

Henseling et al. "Probing the role of threonine and serine residues of *E. Coli* asparaginase II by site directed mutagenisis" Prot. Engin. 5, 785–789 (1992).

Jennings et al. "Analysis of *Escherichia coli* gene encoding L–asparaginase II, ansB, and its . . . " J. Bacteriol. 172, 1491–1498 (Mar. 1990).

Kim et al. "Asparaginase II of *Saccharomyces cerevisiae*" 263, 11948–11953 (Aug. 25, 1988).

Sun et al. "Cloning, nucleotide sequence and expression of the *Bacillus subtilis* ans operon, . . . " J. Bacteriol. 173, 3831–3845 (Jun. 1991).

Jerlstrom et al., "Structure and Expression in *E. Coli* K–12 of the L–Asparaginase I–Encoding ansA Gene and its Flanking Regions," *Gene*, vol. 78 pp. 37–46, (1989).

Bonthron, D.T., "L–Asparaginase IIof *E. Coli* K–12: Cloning, Mapping and Sequencing of the ansB Gene," *Gene*, vol. 91, pp. 101–105, (1990).

(List continued on next page.)

*Primary Examiner*—Nashaat T. Nashed
(74) *Attorney, Agent, or Firm*—Browdy and Neimark

(57) ABSTRACT

Disclosed is a DNA coding for mammalian L-asparaginase. Transformants introduced with the DNA effectively produce desired amounts of mammalian L-asparaginase such as those from humans, guinea pigs, and mice. The DNA is also useful as a probe for screening a DNA coding for desired mammalian L-asparaginase.

7 Claims, 3 Drawing Sheets

OTHER PUBLICATIONS

Yellin et al., "Purification and Properties of Guinea Pig Serum Asparaginase,"*Biochemistry*, vol. 5, No. 5, pp. 1605–1612, (1966).

Kidd, John G., "Regression of transplanted lymphomas induced in vivo by means of normal guinea pig serum." The Journal of Experimental Medicine, vol. 98, pp. 565–583 (1953).

Sambrook, J. et al., "Molecular Cloning, A Laboratory Manual." 2nd Edition, pp. xi–xxxviii (1989).

Gherna, R. ed. et al., Catalogue of Bacteria and Phages, Eighteenth Edition, No. 53323, p. 143 (1992).

Maglott. D.R. ed. et al., Catalogue of Recombinant DNA Materials, 2nd Edition, No. 37254, p. 46 (1991).

| | | | | | | | | | | | | | | | |
|---|---|---|---|---|---|---|---|---|---|---|---|---|---|---|---|
|Thr|Ile|Ala|Glu|Trp|Val|Arg|Val|Ala|Gln|Thr|Ile|Lys|Arg|His|Tyr|104
|Thr|Thr|Thr|Glu|Trp|Val|Gln|Ile|Ala|Gln|Thr|Ile|Glu|Arg|His|Tyr|16

|Glu|Gln|Tyr|His|Gly|Phe|Val|Val|Ile|His|Gly|Thr|Asp|Thr|Met|Ala|120
|---|---|---|---|---|---|---|---|---|---|---|---|---|---|---|---|---|
|Ala|Gln|Tyr|Gln|Gly|Phe|Val|Val|Ile|His|Gly|Thr|Asp|Thr|Met|Ala|32

|Phe|Ala|Ala|Ser|Met|Leu|Ser|Phe|Met|Leu|Glu|Asn|Leu|Gln|Lys|Thr|136
|---|---|---|---|---|---|---|---|---|---|---|---|---|---|---|---|---|
|Phe|Ala|Ala|Ser|Val|Leu|Ser|Ser|Met|Leu|Glu|Asn|Leu|Gln|Lys|Pro|48

|Val|Ile|Leu|Thr|Gly|Ala|Gln|Val|Pro|Ile|His|Ala|Leu|Trp|Ser|Asp|152
|---|---|---|---|---|---|---|---|---|---|---|---|---|---|---|---|---|
|Val|Val|Leu|Thr|Gly|Ala|Gln|Val|Pro|Ile|His|Ala|Leu|Trp|Ser|Asp|64

|Gly|Arg|Glu|Asn|Leu|Leu|Gly|Ala|Leu|Leu|Met|Ala|Gly|Gln|Tyr|Val|168
|---|---|---|---|---|---|---|---|---|---|---|---|---|---|---|---|---|
|Gly|Arg|Glu|Asn|Leu|Leu|Gly|Ala|Leu|Leu|Met|Ala|Gly|Gln|Tyr|Val|80

|Ile|Pro|Glu|Val|Cys|Leu|Phe|Phe|Gln|Asn|Gln|Leu|Phe|Arg|Gly|Asn|184
|---|---|---|---|---|---|---|---|---|---|---|---|---|---|---|---|---|
|Ile|Pro|Glu|Val|Cys|Leu|Phe|Phe|Gln|Asn|Gln|Leu|Phe|Arg|Gly|Asn|96

|Arg|Ala|Thr|Lys|Val|Asp|Ala|Arg|Arg|Phe|Ala|Ala|196
|---|---|---|---|---|---|---|---|---|---|---|---|---|
|Arg|Thr|Thr|Lys|Val|Asp|Ala|Arg|Arg|Phe|Ala|Ala|108

FIG. 2

```
Thr Ile Ala Glu Trp Val Arg Val Ala Gln Thr Ile Lys Arg His Tyr   104
Thr Ile Asp Asp Trp Ile Arg Ile Ala Lys Ile Ile Glu Arg His Tyr   104

Glu Gln Tyr His Gly Phe Val Val Ile His Gly Thr Asp Thr Met Ala   120
Glu Gln Tyr Gln Gly Phe Val Val Ile His Gly Thr Asp Thr Met Ala   120

Phe Ala Ala Ser Met Leu Ser Phe Met Leu Glu Asn Leu Gln Lys Thr   136
Phe Gly Ala Ser Met Leu Ser Phe Met Leu Glu Asn Leu His Lys Pro   136

Val Ile Leu Thr Gly Ala Gln Val Pro Ile His Ala Leu Trp Ser Asp   152
Val Ile Leu Thr Gly Ala Gln Val Pro Ile Arg Val Leu Trp Asn Asp   152

Gly Arg Glu Asn Leu Leu Gly Ala Leu Leu Met Ala Gly Gln Tyr Val   168
Ala Arg Glu Asn Leu Leu Gly Ala Leu Leu Val Ala Gly Gln Tyr Ile   168

Ile Pro Glu Val Cys Leu Phe Phe Gln Asn Gln Leu Phe Arg Gly Asn   184
Ile Pro Glu Val Cys Leu Phe Met Asn Ser Gln Leu Phe Arg Gly Asn   184

Arg Ala Thr Lys Val Asp Ala Arg Arg Phe Ala Ala                   196
Arg Val Thr Lys Val Asp Ser Gln Lys Phe Glu Ala                   196
```

FIG. 3

DNA CODING FOR MAMMALIAN L-ASPARAGINASE

CROSS REFERENCE TO RELATED APPLICATIONS

The present application is a continuation of parent application Ser. No. 09/008,481, filed Jan. 16, 1998, now U.S. Pat. No. 6,087,151 which is a continuation-in-part of application Ser. No. 08/598,369, filed Feb. 8, 1996, now abandoned, the entire contents of both prior applications are hereby incorporated by reference.

BACKGROUND OF THE INVENTION

1. Field of the Invention

The present invention relates to a novel DNA which codes for L-asparaginase, and more particularly, to a DNA which codes for mammalian L-asparaginase.

2. Description of the Prior Art

L-Asparaginase (EC 3.5.1.1), an amidohydrolase which releases L-aspartic acid and ammonia when it acts on L-asparagine, is an enzyme which plays a major role in the metabolism of L-asparagine in plants, animals and microorganisms, and it has been energetically studied on its actual use as an antitumor agent since John G. Kidd had reported the inhibitory activity of L-asparaginase on lymphoma in "The Journal of Experimental Medicine", Vol.98, pp.565–583 (1953). As a result, an L-asparaginase from Escherichia coli is now used as a therapeutic agent for leukemia and lymphoma.

However, the aforesaid L-asparaginase with a satisfactory antitumor activity is only an external protein for humans, and the administration of conventional compositions containing the L-asparaginase to patients frequently causes serious side effects such as hyperergy including anaphylaxis shock, urticaria, edema, wheeze and dyspnea. Therefore, these compositions are inevitably restricted in their administration doses and frequencies-by a large margin, and some proposals to reduce or even diminish such side effects have been made.

As a first proposal, Japanese Patent Laid-Open No.119,082/79 discloses an L-asparaginase from Escherichia coli which is chemically modified by blocking at least 65% of the amino acids of the L-asparaginase with 2-O-substituted polyethylene glycol-4,6-dichloro-S-triazine. As a second proposal, Japanese Patent Laid-Open No.320,684/92 discloses a human L-asparaginase which is obtained from a culture of fibroblasts from human lung, stomach or breast. The first proposal has the advantage that it can use an L-asparaginase from Escherichia coli which is readily preparable on an industrial scale, and has the disadvantage that the control of the modification reaction is difficult and the side effects could not be eliminated. The second proposal has the advantage that, unlike the L-asparaginase from Escherichia coli, human L-asparaginase does not substantially induce antibodies even when administered to patients, and has the disadvantage that the productivity of human fibroblasts is not sufficient as disclosed in Japanese Patent Laid-Open No.320,684/92, so that a relatively large-scale cultivation is inevitable to obtain a satisfactory amount of L-asparaginase.

Recently, recombinant DNA technology has made remarkable progress. Now, even a polypeptide with an incomplete elucidation of its amino acid sequence can be readily prepared in a desired amount, if only a gene coding for the polypeptide is once isolated and decoded for its nucleotide sequence, by preparing a recombinant DNA having a DNA which codes for the polypeptide, introducing the DNA into microorganisms or cells of animals or plants to obtain transformants, and then culturing the transformants.

In view of the foregoing, a gene coding for a mammalian L-asparaginase, preferably, the isolation of a gene coding for human L-asparaginase and the prompt elucidation of its base sequence have been in great demand in this field.

SUMMARY OF THE INVENTION

The object of the present invention is to provide a DNA coding for mammalian L-asparaginase, and the present inventors attained this object by isolating a DNA coding for mammalian L-asparaginase, which is characterized in that it contains nucleotide sequences for either or both amino acid sequences of SEQ ID NOs:1 and 2, as well as in that it is hybridizable with any or all of DNAs with respective nucleotide sequences of SEQ ID NOs:3 to 5.

BRIEF DESCRIPTION OF THE ACCOMPANYING DRAWINGS

FIG. 2 shows homology between partial amino acid sequences of human and mouse L-asparaginases.

FIG. 3 shows homology between partial amino acid sequences of human and guinea pig L-asparaginases.

DETAILED DESCRIPTION OF THE INVENTION

Figure 1:
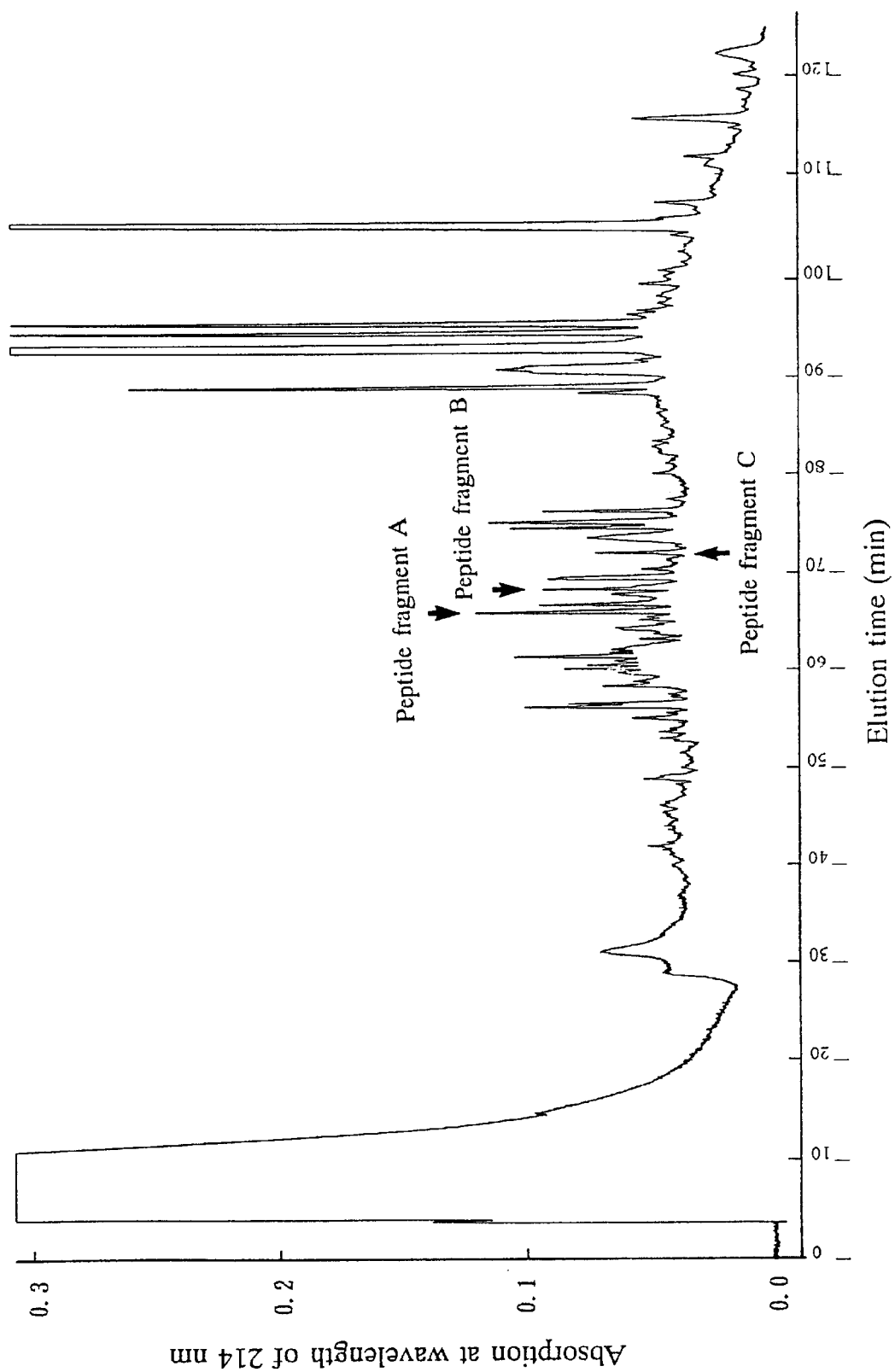
FIG. 1 is a peptide map of guinea pig L-asparaginase.

The DNA according to the present invention expresses the production of mammalian L-asparaginase having a specific amino acid sequence by introducing it into cells or microorganisms to form transformants.

This invention was made based on the finding of a novel DNA which codes for guinea pig L-asparaginase. Although the existence of L-asparaginase in the sera of guinea pigs has been known, the property and feature have not been substantially revealed.

The present inventors isolated a substance with L-asparaginase activity from a guinea pig serum by using purification methods comprising column chromatography as a main technique, and determined its partial amino acid sequences. Based on the sequences, primers were chemically synthesized and subjected to RT-PCR reaction using as a template a mRNA, collected from liver cells of the guinea pig, to obtain a DNA fragment which partially codes for guinea pig L-asparaginase. The present inventors used the fragment as a probe and energetically screened cDNA libraries prepared from the mRNA to obtain a DNA containing the nucleotide sequence of SEQ ID NO:3 consisting of 1,695 base pairs. The decoding of the nucleotide sequence revealed that the guinea pig L-asparaginase consists of 565 amino acids and has the amino acid sequence of SEQ ID NO:6.

With these findings, the present inventors continued studying mRNAs collected from human liver cells and have succeeded in isolating a DNA which codes for human L-asparaginas. The DNA contains the nucleotide sequence of SEQ ID NO:4 which consists of 1,719 base pairs, and the decoding revealed that the DNA encodes the amino acids sequence consisting of 573 amino acids as seen in SEQ ID NO:7.

The present inventors further continued studying mRNAs collected from mouse liver cells based on the above findings and have succeeded in isolating a DNA fragment which partially codes for mouse L-asparaginase. The DNA fragment contains the nucleotide sequence of SEQ ID NO:5 which consists of 324 base pairs, and the decoding revealed that the DNA fragment encodes the amino acid sequence consisting of 108 amino acids as seen in SEQ ID NO:8.

The techniques used to reveal these amino acid sequences and nucleotide sequences of SEQ ID NOs:3–8 are summarized below:

(1) An L-asparaginase was isolated from a guinea pig serum and highly purified by purification methods comprising chromatography as a main technique;

(2) The L-asparaginase was trypsinized, and from the resulting mixture were isolated three peptide fragments which were then determined for amino acid sequence;

(3) A mRNA was collected from the guinea pig liver cells. By using the mRNA as a template, it was subjected to RT-PCR reaction in the presence of primers which had been chemically synthesized based on the above amino acid sequences to generate DNA fragments, which was then screened by a probe that had been chemically synthesized based on those amino acid sequences. Thus, a DNA fragment, which partially encodes the guinea pig L-asparaginase, was obtained;

(4) After labeling the DNA fragment, it was hybridized with a cDNA library, prepared by using the above mRNA as a template, followed by selecting transformants which showed a strong hybridization;

(5) From the transformants a cDNA was collected, determined for its nucleotide sequence, and decoded for its amino acid sequence. Comparison of the decoded amino acid sequence to the above partial amino acid sequences revealed that the guinea pig L-asparaginase has the amino acid sequence of SEQ ID NO:6 and is encoded by the nucleotide sequence of SEQ ID NO:3;

(6) A cDNA library was prepared by using mRNA collected from human liver cells, and a DNA fragment having the nucleotide sequence of SEQ ID NO:3 was prepared, then labeled and hybridized with the cDNA library, followed by selecting transformants which showed a strong hybridization; and (7) From the transformants a cDNA was collected, determined for its nucleotide sequence, and decoded for amino acid sequence, revealing that human L-asparaginase has the amino acid sequence of SEQ ID NO:7 and is encoded by the nucleotide sequence of SEQ ID NO:4.

(8) A mRNA was collected from mouse liver cells. The mRNA as a template was subjected to RT-PCP reaction in the presence of primers which had been chemically synthesized based on the base sequence coding for human L-asparaginase, determined above, to generate DNA fragments, which were then screened by a labelled probe containing the nucleotide sequence of SEQ ID NO:4, coding for human L-asparaginase. Thus, a DNA fragment, which partially encodes mouse L-asparaginase, was obtained; and (9) The DNA fragment was determined for its nucleotide sequence, and decoded for its amino acid sequence, revealing that mouse L-asparaginase contains the amino acid sequence of SEQ ID NO:8 and is encoded by a DNA containing the nucleotide sequence of SEQ ID NO:5.

Comparing the amino acid sequences of SEQ ID NOs:6 to 8 revealed that they share either or both amino acid sequences of SEQ ID NOs:1 and 2. The partial sequences of amino acids 16–19 and 114–118 in SEQ ID NO:6 correspond to SEQ ID NOs:1 and 2, respectively. The partial sequences of amino acids 16–19 and 114–118 in SEQ ID NO:6 correspond to SEQ ID NOs:1 and 2, respectively. The partial sequence of amino acids 26–30 in SEQ ID NO:8 corresponds to SEQ ID NO:2. In addition, the amino acid sequences of SEQ ID NOs:6 to 8 were proved to be highly homologous one another. Between the amino acid sequences of SEQ ID NOs:6 and 7, about 70% homology is observed, and the homology between the amino acid sequence of SEQ ID NO:8 and the partial sequence of amino acids 89–196 in SEQ ID NO:6 or 7 is about 75% or 89%, respectively. Thus the wording "mammalian L-asparaginase" as referred to in the present invention shall mean those which have an amino acid sequence containing either or both amino acid sequences of SEQ ID NOs:1 and 2 and bearing a significantly high homology, usually 70% or higher, to any or all of the amino acid sequences of SEQ ID NOs:6 to 8. As representative examples, guinea pig L-asparaginase containing the amino acid sequence of SEQ ID NO:6, human L-asparaginase containing that of SEQ ID NO:7, mouse L-asparaginase containing that of SEQ ID NO:8, and their homologues can be mentioned. The homologues include those which contain a homologous amino acid sequence to SEQ ID NO:6, 7, or 8 in which one or more amino acids are replaced with different ones or deleted, and those which contain another homologous amino acid sequence to SEQ ID NO:6, 7 or 8 to which one or more different amino acids are added, while retaining the amino acid sequence of SEQ ID NO:1 or 2, a significantly high homology to SEQ ID NO:6, 7, or 8, and the inherent activity without being substantially reduced.

Examples of DNAs coding for the mammalian L-asparaginase as mentioned above are those which contain one of the nucleotide sequences of SEQ ID NOs:3, 4, 5, 9 and 10 and their complementary sequences. In these nucleotides sequences, one or more nucleotides can be replaced with different ones based on the degeneracy of the genetic codes while the amino acid sequences encoded thereby are conserved. To allow the DNAs to actually express in hosts, one or more nucleotides in the nucleotide sequences of the DNAs, which code for the mammalian L-asparaginase as referred to in the present invention, can also be suitably replaced with different ones. In general, respective DNAs coding for highly homologous amino acid sequences, as mentioned above, can remarkably hybridize to one another. Accordingly, the DNA of the present invention, coding for mammalian L-asparaginase, can be characterized in that it is hybridzable with any or all of DNAs with respective nucleotide sequences of SEQ ID NOs:3 to 5 as well as in that it contains nucleotide sequences for either or both amino acid sequences of SEQ ID NOs:1 and 2.

Any natural or artificial preparation of DNAs can be used as the present DNA as far as it contain any one of the nucleotide sequences as mentioned above. The natural sources for the present DNA are, for example, livers of humans, guinea pigs and mice. From these liver cells, the DNA of the present invention containing the nucleotide sequence of SEQ ID NO:3, 4, 5, 9 or 10 can be obtained. The present DNA can be also obtained from livers of mammals other than the above by screening based on the hybridization with DNAs containing the nucleotide sequence of SEQ ID NO:3, 4, 5, 9 or 10. To artificially synthesize the present DNA, it can be chemically synthesized based on the nucleotide sequence of SEQ ID NO:3, 4, 5, 9 or 10, or prepared by inserting DNA coding for the amino acid sequence of SEQ ID NO:6, 7 or 8 into self-replicable vectors to obtain recombinant DNAs, introducing the recombinant DNAs into appropriate hosts to obtain transformants, culturing the transformants, separating the proliferated cells from the cultures, and collecting from the cells the objective plasmids containing the present DNA.

The present DNA thus obtained can be introduced to obtain transformants by conventional methods. The transformants thus obtained produce mammalian L-asparaginase intra- or extra-cellularly when cultured. Unlike conventional L-asparaginase produced from *Escherichia coli* mammalian L-asparaginase has the advantage that it does not substantially cause side effects such as anaphylaxis shock and hyperergy even when repeatedly to patients repeatdly. The mammalian L-asparaginase can be, therefore, selectively used alone or in combination with other drugs to treat acute leukemia, acute lymphocytic leukemia, and mammalian malignant tumors in general including malignant tumors.

The present invention is explained with reference to the following Examples, and the techniques used therein are well known in the art: Examples of such are those described in "*Molecular Cloning A Laboratory Manual, 2nd Edition*" by T. Maniatis et al., published by Cold Spring Harbor Laboratory Press, New York, USA (1989), and in "*Laboratory Manual for Genetic Engineering*" by Masami MURAMATSU, published by Maruzen Co., Ltd., Tokyo, Japan (1988).

EXAMPLE 1
Purification of Guinea Pig L-asparaginase

From one hundred 8-week-old guinea pigs, the blood was collected, pooled, and treated in a conventional manner to obtain 300 ml of serum. Ammonium sulfate was added to the serum to give a saturation degree of 50 w/v%, allowed to stand at 4° C. for 2 hours, and centrifuged at about 8,000 rpm for 30 min. The precipitate was collected, dissolved in 10 mN phosphate buffer (pH 7.0), and dialyzed against a fresh preparation of the same buffer at 4° C. for 18 hours. The dialyzed inner solution was fed to a column packed with 300 ml of "SEPHACRYL S-300", a gel for gel filtration column chromatography commercialized by Pharmacia LKB Biotechnology AB, Uppsala, Sweden, which had been equilibrated with a fresh preparation of the same buffer, followed by feeding to the column a fresh preparation of the same buffer.

Fractions corresponding to a molecular weight of about 150,000 daltons were collected, pooled, and fed to a column packed with "DEAE-5PW", a gel for high-performance liquid chromatography commercialized by Tosoh Corporation Tokyo, Japan, which had been equilibrated with 20 mM phosphate buffer (pH 7.0), followed by washing the column with a fresh preparation of the same buffer and feeding to the column at a flow rate of 13 ml/min a linear gradient buffer of sodium chloride increasing from 0 M to 1 M in 20 mM phosphate buffer (pH 7.0). About 120 ml fractions eluted at a concentration of about 0.25 M of sodium chloride were collected, pooled and dialyzed against distilled water at 4° C. for 4 hours. The dialyzed inner solution was fed to a column packed with 100 ml "BLUE SEPHAROSE CL-6B", a gel for affinity chromatography commercialized by Pharmacia LKB Biotechnology AB, Uppsala, Sweden, followed by feeding to the column with a fresh preparation of the same buffer to elute guinea pig L-asparaginase.

Fractions containing the L-asparaginase were collected, pooled and concentrated, and the concentrate was fed to a column packed with "HILOARD SUPERDEX 200", a gel for gel filtration chromatography commercialized by Pharmacia LKB Biotechnology AB, Uppsala, Sweden, followed by feeding to the column with a fresh preparation of the same buffer. Fractions corresponding to a molecular weight of about 150,000 daltons were collected, pooled and concentrated to obtain about 400 µg of the guinea pig L-asparaginase with a specific activity of about 10 units/mg protein per guinea pig.

Throughout the present specification, the activity of L-asparaginase is assayed as follows and expressed with units: Distribute a sample to a 96-well microplate in a volume of 160 µl/well, and add to each well a 40 µl solution containing 1.4 mg/ml of L-asparagine dissolved in 50 mM phosphate buffer (pH 7.0). Incubate the microplate at 37° C. for 10–30 min and quantify the released L-aspartic acid by an amino acid analyzer. Provide a system using an L-asparaginase from *Escherichia coli* which had been diluted to give a concentration of 1.0, 0.5 or 0.25 units/ml, and similarly as above treat the system and quantify the released L-aspartic acid. Plot the measurements to draw a working line. To estimate the activity of the sample, plot the L-aspartic acid content in the sample system. One unit activity of L-asparaginase is defined as the amount of a polypeptide having an L-asparaginase activity that releases one µmol ammonia from L-asparagine per min when allowed to react under the above conditions.

EXAMPLE 2
Partial Amino Acid Sequence of Guinea Pig L-asparaginase

A portion of the aqueous solution containing the purified L-asparaginase in Example 1 was placed in a container and concentrated to give about 50 µl of concentrate. To the concentrate was added 25 µl of a mixture solution consisting of 3 w/v% sodium dodecyl sulfate (SDS), 60 w/v% glycerol and 60 mg/ml dithiothreitol, and the resulting solution was incubated at 50 C for 30 min, transferred onto 10 w/v% polyacrylamide gels, and electrophoresed in a conventional manner. The resulting gels were successively soaked for staining in 50 v/v% aqueous methanol containing 0.1 w/v% Coomassie Brilliant Blue R250 and 10 v/v% acetic acid, destained by washing repeatedly with 12 v/v% aqueous methanol containing 7 v/v M acetic acid, and soaked in distilled water for 18 hours, followed by cutting out and lyophilizing the stained gel bands.

The dried gel bands were soaked in a 0.6 ml mixture solution consisting of 2 µg/ml "TPCK TRYPSIN", a trypsin preparation commercialized by Sigma Chemical Company, St. Louis, Missouri, USA, 0.5 mM calcium chloride and an aqueous solution of 0.02 v/v% TWEEN 20, and incubated at 37° C. for 18 hours to trypsinize the L-asparaginase. The trypsinized product was centrifuged and separated to obtain a supernatant and a precipitate which was then soaked in one ml of one v/v% aqueous trifluoroacetic acid solution containing 0.001 v/v% TWEEN 20, stirred at ambient temperature for 4 hours, and centrifuged to obtain a supernatant. The resulting precipitate was successively treated similarly as above with a 70 v/v% aqueous trifluoroacetic acid solution containing 0.001 v/v% TWEEN 20, and an acetonitrile solution containing 0.001 v/v% TWEEN 20 and 50 v/v% trifluoroacetic acid to obtain a supernatant which was then mixed with the above supernatant. The mixed solution was concentrated up to give 250 µl which was then centrifugally filtered.

The aqueous solution containing the peptide fragments thus obtained was fed to a column of "HPLC ODS-120T", a gel for high-performance liquid column chromatography commercialized by Tosoh Corporation, Tokyo, Japan. The column was washed with 0.1 v/v% aqueous trifluoroacetic acid solution and fed with a linear gradient buffer of aqueous acetonitrile increasing from 0 v/v% to 70 v/v% in 0.1 v/v% aqueous trifluoroacetic acid solution at a flow rate of 0.5 ml/min. Fractions eluted at about 66 min, about 69 min and about 72 min after starting the feeding (hereinafter designated as "peptide fragment A", "peptide fragment B" and "peptide fragment C", respectively) were collected. The elution pattern, i.e, a peptide map of the guinea pig's L-asparaginase, is shown in FIG. 1.

By using "MODEL 473A", a protein sequencer commercialized by Perkin-Elmer Corp., Norwalk, USA, these peptide fragments A, B and C were studied in a conventional manner, is revealed that they have the amino acid sequences of SEQ ID NOs:11 to 13.

EXAMPLE 3

Total Amino Acid Sequence of Guinea Pig L-asparaginase and Base Sequence Coding For it Example 3-1
Preparation of Total RNAs Three g of wet cells of a guinea pig liver, prepared in a conventional manner, was weighed, suspended in 20 ml of a 6 M aqueous guanidine isothiocyanate solution containing 10 mM sodium citrate (pH 7.0) and 0.5 w/v% SDS, and disrupted by a homogenizer. Into a 35-ml centrifuge tube was injected 25 ml of a mixture solution of 5.7 M cesium chloride and 0.1 M EDTA (pH 7.5), and the disrupted cells were overlaid on the solution, followed by centrifuging the tube at 25,000 rpm and at 20° C. for 20 hours. A fraction containing RNAs was collected from the tube, transferred to another 15-ml centrifuge tube, mixed with an equal amount of chloroform/butanol (=4:1 by volume), stirred for 5 min, and centrifuged at 10,000 g×10 min and at 4° C. The resulting water layer was collected, mixed with 2.5-fold volumes of ethanol, and allowed to stand at −20° C. for 2 hours to precipitate the total RNAs. The precipitated RNAs were washed with 75 v/v% ethanol and dried to obtain the total RNAs in a yield of about 4 mg.

Example 3-2
Preparation of DNA Fragment Partially Coding For Guinea Pig L-asparaginase To one µg of the total RNAs prepared in Example 3-1 were added 4 µl of 25 mM magnesium chloride, 2 µl of 10×PCR buffer consisting of 100 M Tris-HCl buffer (pH 8.3) and 500 mM potassium chloride, 8 µl of one mM dNTP mix, one µl of one unit/µl of an RNase inhibitor, one µl of 2.5 units/µl of a reverse transcriptase, one µl of 2.5 µM of a random hexamer, and a volume of sterile distilled water sufficient to bring the total volume to 20 µl. The mixture solution was placed into a 0.5-ml test tube and in a conventional manner successively incubated at 25° C. for 10 min, at 42° C. for 30 min, at 99° C. for 5 min, and at 5° C. for 5 min to conduct an enzymatic reverse transcriptase reaction. Thus, an aqueous solution containing a first strand cDNA was obtained.

Twenty µl of the aqueous solution was mixed with 4 µl of 25 mM magnesium chloride, 8 µl of 10×PCR buffer consisting of 100 mM Tris-HCl buffer (pH 8.3) and 500 mM potassium chloride, 0.5 µl of 2.5 units/ml amplitaq DNA polymerase, one µmol of primer 1 as a sense primer, one µmol of a primer 2 as an antisense primer, and a volume of sterile distilled water sufficient to bring the total volume to 100 µl. The mixture solution was in a conventional manner successively allowed to react at 94° C. for one min, at 42° C. for 2 min, and at 72° C. for 3 min, and these sequential reaction steps were repeated 40 times to amplify a DNA fragment, which partially encodes the guinea pig L-asparaginase, by using the first strand cDNA as a template. The primers 1 and 2 are oligonucleotides, which were chemically synthesized based on the amino acid sequences of Gly-Met-Gln-Ser-Lys (amino acids 12–16 in SEQ ID NO:12) and Tyr-Pro-Gly-Ile-Pro-Ala (amino acids 2–7 in SEQ ID NO:11), and have nucleotide sequences represented by 5'-GGNATGCARWSNAAR-3' (SEQ ID NO:15) and 5'-GCNGGDATNCCNGGRTA-3' (SEQ ID NO:16), respectively.

The PCR reaction product thus obtained was sampled and analyzed by conventional Southern hybridization method as follows. The sample was electrophoresed in a 2 w/v% agarose gel to effect fractionation, followed by press-blotting the gel with 0.4 N sodium hydroxide to transfer and fix DNAs onto a nylon film. The film was successively washed with 2×SSC, air-dried, soaked in a mixed solution for prehybridization containing 5×SSPE, 5×Denhardt's solution, 0.5 w/v% SDS and 100 µg/ml of a denatured salmon sperm DNA, and incubated in the solution at 65° C. for 3 hours. An oligonucleotide as probe 1, having a nucleotide sequence represented by 5'-TTYATGYTNGARAAYYT-3' (SEQ ID NO:17), was chemically synthesized based on the amino acid sequence of Phe-Met-Leu-Glu-Asn-Leu (amino acids 2–7 in SEQ ID NO:13), and labelled with [γ-$^{32}$P]ATP and T4 polynucleotide kinase. The above nylon film was successively soaked in a mixed solution containing one µmol of the probe 1, 5×SSPE, 5×Denhardt's solution, 0.5 W/v% SDS, and 100 µg/ml of a denatured salmon sperm DNA, incubated at 42° C. for 24 hours to effect hybridization, washed with 6×SSC at ambient temperature, and autoradiographed in a conventional manner, revealing that the formed PCR product contained the objective DNA fragment.

The remaining PCR product was admixed with 50 ng "pT7 BLUE T", a plasmid vector commercialized by Novachem Ltd., Tel Aviv, Israel, and an adequate amount of T4 DNA ligase, admixed with 100 mM ATP up to give a final concentration of one mM, and incubated at 16° C. for 18 hours to insert the above DNA fragment into the plasmid vector. The recombinant DNA thus obtained was introduced into "NoVa Blue strain", a microorganism of the species *Escherichia coli* commercialized by Novachem Ltd., Tel Aviv, Israel, to obtain a transformant which was then inoculated into a plate medium containing 10 g/l bacto-tryptone, 5 g/l bacto-yeast extract, 2.5 g/l sodium chloride, 15 g/l bacto-agar, 100 mg/l ampicillin, 40 mg/l X-Gal and 23.8 mg/l isopropyl-p-D-thiogalactopyranoside (hereinafter abbreviated as "IPTG"), and incubated at 37° C. for 24 hours to form colonies. According to conventional colony hybridization method, a nylon film was placed on the surface of the plate medium, allowed to stand for about 30 sec to transfer the colonies onto the film, then the film was detached from the plate medium and soaked in a mixed solution containing 0.5 M sodium hydroxide and 1.5 M sodium chloride for 7 min to lyse the cells. Thereafter, the nylon film was successively soaked in 0.5 M Tris-HCl buffer (pH 7.2) containing 1.5 M sodium chloride for 3 min, washed with 2×SSC, soaked in 0.4 M sodium hydroxide for 20 min, washed with 5×SSC, air-dried, soaked in a mixed solution for prehybridization containing 5×SSPE, 5×Denhardt's solution, 0.5 w/v SDS and 100 µg/ml of a denatured salmon sperm DNA, and incubated at 42° C. for 24 hours. The probe 1 was hybridized with the nylon film in a conventional manner, and the resultant was washed with 6×SSC and autoradiographed similarly as above, followed by collecting from the plate medium a transformant which strongly hybridized with probe 1.

The transformant was inoculated into L-broth (pH 7.2) containing 100 µg/ml ampicillin and cultured at 37° C. for 18 hours, followed by collecting cells from the culture and collecting the a recombinant DNA by conventional alkali-SDS method. The dideoxy method revealed that the recombinant DNA contained a DNA fragment of a nucleotide sequence corresponding to bases 61–746 in SEQ ID NO:3.

Example 3-3

Preparation of mRNA 0.05 ml of an aqueous solution containing 500 μg of the total RNAs in Example 3-1 was placed in a container, into which was poured 0.5 ml of 10 mM Tris-HCl buffer (pH 7.5) containing one mM EDTA and 0.1 w/v% SDS up to give a total volume of one ml. To the mixture solution was added one ml of "OLIGOTEX-dT300 SUPER", an oligo(dT)$_{30}$ latex commercialized by Nippon Roche K.K., Tokyo, Japan, and the resulting mixture was incubated at 65° C. for 5 min to denature the contents and promptly cooled in an ice-chilled bath for 3 min. 0.2 ml of 5 M sodium chloride was added to the cooled solution, and the resulting solution was incubated at 37° C. for 10 min and centrifuged at 10,000 rpm and at 25° C. for 10 min, followed by removing a supernatant to obtain a pellet-like precipitate, suspending the precipitate in 0.5 ml sterile distilled water, incubating the suspension at 65° C. for 5 min to extract the objective mRNA from the "OLIGOTEX-dT300 SUPER". The yield of the mRNA was about 5 μg.

Example 3-4

Preparation of cDNA Library

By using "cDNA SYNTHESIZING SYSTEM PLUS", a cDNA cloning kit commercialized by Amersham Corp., Div., Amersham International, Arlington Heights, USA, a cDNA library was prepared from the mRNA in Example 3-3. Into a 1.5-ml reaction tube were successively poured a 4 μl solution for synthesizing a first strand, one μl sodium pyrophosphate, one μl human placenta ribonuclease inhibitor, 2 μl dideoxynucleotide triphosphate mixture, and one μl oligo dT primer, then mixed with 5 μl of the mRNA prepared in Example 3-3 and a volume of sterile distilled water sufficient to bring the total volume to 19 μl. To the resulting solution was added one μl of a solution containing 20 units of a reverse transcriptase, followed by incubation at 42° C. for 40 min to obtain a reaction mixture containing a first strand cDNA.

The reaction mixture was successively admixed with a 37.5 μl solution for synthesizing a second strand cDNA, 0.8 units of ribonuclease H from *Escherichia coli*, and 23 units of DNA polymerase I, increased its volume up to 100 μl by the addition of sterile distilled water, incubated at 12° C. for 60 min and at 22° C. for 60 min, admixed with 2 units T4 DNA polymerase, and further incubated at 37° C. for 10 min to obtain a solution containing the objective second strand cDNA. To the solution thus obtained was added 4 μl of 0.25 M EDTA (pH 8.0) to suspend the reaction, followed by extracting with phenol/chloroform, precipitating the objective cDNA with ethanol, and then collecting the cDNA.

Two μl L/K buffer, 250 μmol Eco RI adapter and 2.5 units of T4 DNA ligase were added to the above cDNA in the order, presented and the volume of the mixed solution was increased up to 20 μl with sterile distilled water, and incubated at 15° C. for 16 hours to ligate the Eco RI adaptor to both ends of the cDNA. The reaction mixture was mixed with 2 μl of 0.25 M EDTA (pH 8.0) to inactivate the remaining enzymes, and the intact Eco RI adaptor was removed in a conventional manner by molecular sieve chromatography. To the resultant were added 40 μl L/K buffer and 80 units of T4 polynucleotide kinase, and the volume of the mixture was increased up to 400 μl with sterile distilled water, followed by incubating the mixture solution at 37° C. for 30 min to phosphorylate the 5'-terminus of Eco RI adaptor, and precipitating the reaction mixture with phenol/chloroform and ethanol to obtain a DNA. The DNA was mixed with 1.5 μl L/K buffer containing an adequate amount of λgt10 arm and with 2.5 units of T4 DNA ligase, increased to a volume of 15 μl with sterile distilled water, incubated at 15° C. for 16 hours, and treated with conventional in vitro packaging method to obtain a phage containing a recombinant λDNA.

Example 3-5

Cloning of Recombinant DNA

*Escherichia coli* NM514 strain, commercialized by Amersham Corp., Div., Amersham International, Arlington Heights, USA, was in a conventional manner infected with the phage in Example 3-4, inoculated into an agar plate (pH 7.0) containing 10 g/l bacto-tryptone, 5 g/l bacto-yeast extract, 10 g/l sodium chloride, and 15 g/l bacto-agar, and incubated at 37° C. for 10 hours to form plaques. A nylon film was placed on the surface of the agar plate and allowed to stand for about 30 sec to transfer the plaques onto the film, then detached from the plate, and successively and repeatedly soaked in an aqueous solution containing 0.5 M sodium hydroxide and 1.5 M sodium chloride for 7 min and in 0.5 M Tris-HCl buffer (pH 7.0) containing 1.5 M sodium chloride for 3 min. The nylon film was successively rinsed with 5×SSC, air-dried, soaked in 0.4 N sodium hydroxide for 20 min, rinsed with 2×SSC, air-dried, soaked in a mixed solution containing 5×SSPE, 5×Denhardt's solution, 0.5 w/v% SDS and 100 μg/ml of a denatured salmon sperm DNA, and incubated at 65° C. for 3 hours. The DNA fragment in Example 3-2 was labeled with $^{32}$P using "REDIPRIME DNA LABELLING SYSTEM" Amersham Corp., Div., Amersham International, Arlington Heights, USA, to obtain a probe 2, and an adequate amount of which was hybridized at 65° C. for 20 hours by incubating in a mixed solution containing 5×SSPE, 5×Denhardt's solution, 0.5 w/v% SDS and 100 μg/ml of a denatured salmon sperm DNA. The nylon film was successively soaked in and rinsed with 2×SSC at 65° C. for 20 min and 0.2×SSC at 65° C. for 20 min, and subjected to autoradiography, followed by selecting a phage DNA clone which strongly hybridized with the probe 2.

The clone was amplified in *Escherichia coli*, and a recombinant DNA was extracted from the microorganism. The recombinant DNA was cleaved by Eco RI, a restriction enzyme, and plasmid vector pUCl9 (ATCC 37254) was cleaved with the same restriction enzyme. The formed DNA- and plasmid-fragments were in a conventional manner ligated with a DNA ligase to obtain a recombinant DNA which was then introduced into *Escherichia coli* JM109 strain (ATCC 53323) by conventional competent cell method to obtain a transformant.

Example 3-6

Determination of Nucleotide Sequence of DNA and Amino Acid Sequence of Protein

The transformant in Example 3-5 was inoculated into L-broth (pH 7.2) containing 50 μg/ml ampicillin and cultured at 37° C. for 18 hours under shaking conditions. From the culture the proliferated transformants were collected and treated with conventional alkali-SDS method to obtain a recombinant DNA containing the DNA according to the present invention. The recombinant DNA was analyzed on an automatic sequencer using a fluorophotometer and the results revealed that it contained the nucleotide sequence of SEQ ID NO:9, and the decoding of its predicted amino acid sequence indicated that it encodes the amino acid sequence. The amino acid sequence has the partial amino acid sequence of SEQ ID NO:12 or 11 in its partial amino acid sequence consisting of amino acids positioning at 10–25 or 243–253. This indicates that the DNA of SEQ ID NO:3 codes for guinea pig L-asparaginase containing the amino acid sequence of SEQ ID NO:6.

In Example 4, a cDNA coding for human L-asparaginase is collected from a mRNA from human liver by using the DNA of SEQ ID NO:3 as a probe. The total amino acid sequence of human L-asparaginase was determined by analyzing and decoding the nucleotide sequence of the cDNA.

EXAMPLE 4
Total Amino Acid Sequence of Human L-asparaginase and Nucleotide Sequence of DNA Which Codes For Human L-asparaginase Example 4-1
Preparation of cDNA Library By using ""cDNA SYNTHESIZING SYSTEM PLUS", a cDNA cloning kit commercialized by Amersham Corp., Div., Amersham International, Arlington Heights, USA, a cDNA library was prepared from a poly (A) modified human liver RNA commercialized by Clontech Laboratories, Inc., California, USA. Into a 1.5-ml reaction tube were poured 10 µl of a first strand synthesizing solution, 2.5 µl of one mM sodium pyrophosphate, 2.5 µl of one µg/µl of a human placenta ribonuclease inhibitor, 5 µl of one µg/µl deoxynucleotide triphosphate mixture, and 2.5 µl of one µg/µl oligo dT primer, then mixed with 5 µg of a poly (A) modified human liver RNA. The volume of the mixture was increased to 45 µl with sterile distilled water, then mixed with a 5 µl solution containing 100 units of a reverse transcriptase, and incubated at 42° C. for 40 min to obtain a reaction product containing a first strand cDNA.

To the reaction product were added 93.5 µl of a cDNA synthesizing solution, 4 units of ribonuclease H from *Escherichia coli*, and 115 units of DNA polymerase I, and the volume of the was increased to 250 µl with sterile distilled water, then successively incubated at 12° C. for 60 min, at 22° C. for 60 min, and at 70° C. for 10 min, mixed with 10 units of T4 DNA polymerase, and further incubated at 37° C. for 10 min, followed by suspending the reaction with the addition of 100 µl of 0.25 M EDTA (pH 8.0). The reaction product was in a conventional manner extracted with phenol/chloroform, and the extract was precipitated with ethanol to obtain a second strand cDNA.

The second strand cDNA thus obtained was mixed with 2 µl L/K buffer (pH 8.0), 250 µmol Eco RI adaptor, and 2.5 units T4 DNA ligase, and the volume of the mixture was increased to 20 µl with sterile distilled water and incubated at 15° C. for 16 hours to ligate the Eco RI adaptor to both ends of the cDNA. The reaction was suspended by the addition of 2 µl of 0.25 M EDTA (pH 8.0). Intact Eco RI adaptor was removed from the reaction mixture by molecular sieve chromatography, and the remaining reaction mixture was mixed with 40 µl of L/K buffer (pH 8.0) and 80 units of T4 polynucleotide kinase, increased its volume to 400 µl with sterile distilled water, incubated at 37° C. for 30 min to phosphorylate the 5'-terminus of the Eco RI adaptor, and extracted with phenol/chloroform. The extract was precipitated with ethanol to collect cDNA which was then mixed with 1.5 µl of L/K buffer (pH 8.0) containing an adequate amount of Xgt 10 arm and 2.5 units of T4 DNA ligase, and the volume of the mixture was increased to 15 µl with sterile distilled water, incubated at 15° C. for 16 hours, and applied with the in vitro packaging to obtain a phage containing a recombinant λDNA.

Example 4-2
Cloning of Recombinant DNA

*Escherichia coli* NM514 strain was infected with the phage in Example 4-1, inoculated into an agar plate (pH 7.0) containing 10 g/l bacto-tryptone, 5 g/l bacto-yeast extract, 10 g/l sodium chloride and 15 g/l bacto-agar, and incubated at 37° C. for 10 hours to form plaques. A nylon film was placed on the surface of the agar plate, allowed to stand for about 30 sec to transfer the plaques onto the film, detached from the plate, and successively and repeatedly soaked in an aqueous solution containing 0.5 M sodium hydroxide and 1.5 M sodium chloride for 7 min, and 0.5 M Tris-HCl buffer (pH 7.0) containing 1.5 M sodium chloride for 3 min. The film was rinsed with 2×SSC, air-dried, soaked in a mixed solution containing 5×SSPE, 5×Denhardt's solution, 0.5 w/v % SDS and 100 µg/ml of a denatured salmon sperm, and incubated at 65° C. for 3 hours.

To clone a recombinant DNA, probe 3 was prepared by labelling the DNA fragment of SEQ ID NO:3 with "REDIPRIME DNA LABELLING SYSTEM": Twenty-five ng of a DNA fragment, obtained by the method in Example 3-5, was placed in a 1.5-ml reaction tube, mixed with sterile distilled water to obtain 45 µl solution which was then heated at 95° C. for 3 min, and transferred to another reaction tube. Five µl of [α-$^{32}$P]dCTP solution was added to the tube, and the DNA fragment was labelled by incubating at 37° C. for 30 min. The reaction mixture containing the labelled DNA fragment was treated with conventional molecular sieve chromatography to remove intact [α-$^{32}$µ]dCTP. Thus the probe 3 was obtained.

The nylon film was incubated at 50° C. for 20 hours in a mixed solution containing an adequate amount of the probe 3, 5×SSPE, 5×Denhardt's solution, 0.5 w/v% SDS, and 100 µg/ml of a denatured salmon sperm to hybridize the probe, then successively incubated in 6×SSC at ambient temperature for 20 min, incubated in 2×SSC at ambient temperature for 20 min, washed and autoradiographed, followed by selecting a phage clone which strongly hybridized with probe 3. The clone was in a conventional manner amplified in *Escherichia coli*, then a recombinant DNA was extracted from the microorganism. The recombinant DNA was cleaved with Eco RI, a restriction enzyme, and in a conventional manner ligated by a DNA ligase with the DNA fragment and a plasmid fragment, obtained by cleaving plasmid vector pUC19 (ATCC 37254) with the restriction enzyme. The recombinant DNA was introduced into *Escherichia coli* JM109 strain (ATCC 53323) by conventional competent cell method to obtain a transformant.

Example 4-3
Determination of Nucleotide Sequence of DNA Which Codes For Human L-Asparaginase, and Its Total Amino Acid Sequence The transformant in Example 4-2 was inoculated into L-broth (pH 7.2) containing 50 µg/ml ampicillin and cultured at 37° C. for 18 hours under shaking conditions. From the culture the proliferated transformants were collected, treated with conventional alkali-SDS method to obtain the present recombinant DNA according to the present invention. The analysis of the recombinant DNA on an automatic sequencer using a fluorophotometer revealed that it has the nucleotide sequence of SEQ ID NO:10. An amino acid sequence estimable from the base sequence is along with SEQ ID NO:10, and this indicates that the DNA of SEQ ID NO:4 codes for human L-asparaginase containing the amino acid sequence of SEQ ID NO:7. Comparison of the amino acid sequences of SEQ ID NOs:6 and 7 revealed that they have about 70% homology.

In Example 5, a cDNA partially coding for mouse L-asparaginase is collected after effecting RT-PCR reaction with a mRNA from mouse liver as a template in the presence of primers chemically synthesized based on the nucleotide sequence of SEQ ID NO:4. By analyzing and decoding the nucleotide sequence of the cDNA, a partial amino acid sequence of mouse L-asparaginase is determined.

EXAMPLE 5
Partial Amino Acid Sequence of Mouse L-asparaginase and the Nucleotide Sequence Coding For it Three g of fresh liver cells from 8-week-old CD-1 mice, prepared by a conventional method, were treated similarly as in Example 3-1 to obtain about 4 mg of a total RNA. One µg of the total RNA was treated similarly as in Example 3-2 to obtain 20 µl of an aqueous solution with a first strand cDNA. The aqueous solution was admixed with 4 µl of 25 mM magnesium chloride, 8 µl of 10×PCR buffer consisting of 100 mM Tris-HCl buffer (pH 8.3) and 500 mM potassium chloride, 0.5 µl of 2.5 units/µl amplitaq DNA polymerase, adequate amounts of primer 3 as a sense primer and primer 4 as an antisense primer, and a volume of sterile distilled water sufficient to bring the total volume to 100 µl: The primer 3 was an oligonucleotide chemically synthesized in usual manner, which had the nucleotide sequence of SEQ ID NO:18 that corresponds to a sequence of nucleotides 247–264 in SEQ ID NO:4, and the primer 4 was another oligonucleotide chemically synthesized in usual manner, which had the nucleotide sequence of SEQ ID NO:19 that is complementary to the sequence of nucleotide 589–606 in SEQ ID NO:4. The resulting mixture was subjected to 40 times of successive incubations at 94° C. for 1 min, 40° C. for 2 min, and 72° C. for 3 min, in the given order, to effect PCR reaction.

A sample of the PCR reaction product thus obtained was electrophoresed in 2 w/v% agarose gel in the usual manner to effect fractionation and analyzed by Southern hybridization method under the conditions according to those in Example 3-2 except for using probe 4 as a probe. Probe 4 was obtained by labelling a DNA fragment with the nucleotide sequence of SEQ ID NO:4 for human L-asparaginase by similar procedure for preparing the probe 3 in Example 4-2, a temperature of 50° C. for hybridization, and 2×SSC following 6×SSC to wash a nylon film after hybridization. As a result, t he above PCR reaction product was confirmed to contain a DNA fragment of about 360 base pairs which strongly hybridize with the DNA having the nucleotide sequence of SEQ ID NO:4.

Similarly as i n Example 3-2, another sample of the above PCR reaction product was inserted into "pT7 BLUE T", a plasmid vector commercialized by Novachem Ltd., Tel Aviv, Israel, to obtain recombinant DNAs, and the recombinant DNAS were introduced into "NoVa Blue strain", a microorganism of the species *Escherichia coli* commercialized by Novachem Ltd., Tel Aviv, Israel, to obtain transformants which were then cultured on a plate medium to form colonies. The colonies were transfered to nylon films and subjected to colony hybridization method under the conditions according to those in Example 3-2 except for using probe 4 as the probe, a temperature of 50° C. for hybridization, and 2×SSC following 6×SSC to wash the nylon film after hybridization. A transformant with which probe 4 strongly hybridized was collected and cultured in the usual manner in L-broth medium containing 100 µg/ml ampicillin, and a recombinant DNA was collected from the resulting culture by conventional alkali-SDS method. A sample of the recombinant DNA was analyzed by the dideoxy method, which revealed that the recombinant DNA contains the nucleotide sequence of SEQ ID NO:14 and codes for the amino acid sequence shown along with SEQ ID NO:14. SEQ ID NOs:5 and 8 show the nucleotide and the amino acid sequences of mouse, respectively, determined in t his Example.

Homology between the amino acid sequences of mouse, determined in this Example, and of human L-asparaginase, determined in Example 4-3, were studied in the usual manner. As shown in FIG. 2, the amino acid sequence of SEQ ID NO:8 of mouse was proved to bear about 89% homology to a partial amino acid sequence of human L-asparaginase, consisting of amino acids 89–196 in SEQ ID NO:7. For reference, FIG. 3 shows that the partial amino acid sequence of human L-asparaginase, consisting of amino acids 89–196 in SEQ ID NO:7, bears about 77% homology to a partial amino acid sequence of guinea pig L-asparaginase consisting of amino acids 89–196 in SEQ ID NO:6. These results mean that the amino acid sequences of SEQ ID NO:8 is a partial amino acid sequence of mouse L-asparaginase and that the nucleotide sequence of SEQ ID NO:5 codes for the partial amino acid sequence. In addition, the results of the colony hybridization in this Example indicate that the DNA with the nucleotide sequence of SEQ ID NO:4, coding for human L-asparaginase, did not hybridize with an *Escherichia coli* genomic DNA which contains a nucleotide sequence coding for *Escherichia coli* L-asparaginase.

The results of this Example and Examples 3 and 4 indicate that mammalian L-asparaginases share either or both amino acid sequences of SEQ ID NOs:1 and 2 and are highly homologous in their amino acid sequences, in particular, L-asparaginases of rodents such as guinea pigs and mice and of other mammals more closely related to humans usually contain an amino acid sequence bearing a 70% or higher homology to the amino acid sequence of SEQ ID NO:7. Furthermore, these results indicate that respective DNAs coding for such mammalian L-asparaginases can strongly hybridize one another.

As it is described above, the present invention is based on the finding of a novel DNA coding for mammalian L asparaginase. The application of conventional recombinant DNA technology to the present DNA facilitates the production of a desired amount of mammalian L-asparaginase including a human L-asparaginase which could not have been readily obtained. In addition, the present invention is also based on the original findings that the DNAs coding for mammalian L-asparaginases respectively have specific nucleotide sequences, as well as that such DNAs are homologous, usualy 70% or higher, and can hybridize to one another. Accordingly, the DNA of the present invention has actual advantages that facilitate the attainment of not only a desired amount of mammalian L-asparaginase but also a DNA coding for L-asparaginase of a desired mammal by using as a probe the DNA of the present invention.

The present invention with these outstanding effects would greatly contribute to this filed.

While there has been described what is at present considered to be the preferred embodiments of the invention, it will be understood the various modifications may be made therein, and it is intended to cover in the appended claims all such modifications as fall within the true spirit and scope of the invention.

What is claimed is:

1. An isolated DNA encoding for mammalian L-asparaginase, which comprises nucleotide sequences encoding for either or both the amino acid sequences of SEQ ID NOs:1 and 2, and which is hybridizable to any of the nucleotide sequences of SEQ ID NOs:3 to 5 at 42° C. in a solution of 5 ×SSPE, 5×Denhardts solution, 0.5 w/v% SDS, and 100 µg/ml denatured salmon sperm DNA, wherein said mammalian L-asparaginase has an amino acid sequence having at least 70% of its residues identical to the corresponding residues of the amino acid sequence of SEQ ID NO:7.

2. The isolated DNA according to claim 1, which comprises a nucleotide sequence encoding an amino acid sequence selected from the group consisting of SEQ ID NOs:6 to 8.

3. The isolated DNA according to claim 1, wherein, based on the degeneracy of the genetic code, one or more nucleotides in a nucleotide sequence selected from the group consisting of SEQ ID NOs:3, 4, 5, 9 and 10 are replaced with different nucleotides without altering the encoded amino acid sequences.

4. The isolated DNA according to claim 1, which encodes a human, guinea pig or mouse L-asparaginase.

5. A recombinant vector comprising the isolated DNA of claim 1.

6. A host cell transformed with the recombinant vector of claim 5.

7. A method for producing a mammalian L-asparaginase, comprising the steps of:

transforming a host cell with a DNA in accordance with claim 1 in a manner such that said transformed host cell can produce a mammalian L-asparaginase intracellularly or extracelluarly when cultured;

culturing said transformed host cell to produce said mammalian L-asparaginase; and recovering said produced mammalian L-asparaginase.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Thr Gly Gly Thr
1

(2) INFORMATION FOR SEQ ID NO:2:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

His Gly Thr Asp Thr
1               5

(2) INFORMATION FOR SEQ ID NO:3:

(i) SEQUENCE CHARACTERISTICS:
       (A) LENGTH: 1695 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO:3:

| | | | | | |
|---|---|---|---|---|---|
| ATGGCGCGCG | CATCAGGCTC | CGAGAGGCAC | CTGCTGCTCA | TCTACACTGG | CGGCACTTTG | 60 |
| GGCATGCAGA | GCAAGGGCGG | GGTGCTCGTC | CCCGGCCCAG | GCCTGGTCAC | TCTGCTGCGG | 120 |
| ACCCTGCCCA | TGTTCCATGA | CAAGGAGTTC | GCCCAGGCCC | AGGGCCTCCC | TGACCATGCT | 180 |
| CTGGCGCTGC | CCCCTGCCAG | CCACGGCCCC | AGGGTCCTCT | ACACGGTGCT | GGAGTGCCAG | 240 |
| CCCCTCTTGG | ATTCCAGCGA | CATGACCATC | GATGATTGGA | TTCGCATAGC | CAAGATCATA | 300 |
| GAGAGGCACT | ATGAGCAGTA | CCAAGGCTTT | GTGGTTATCC | ACGGCACCGA | CACCATGGCC | 360 |
| TTTGGGGCCT | CCATGCTGTC | CTTCATGCTG | GAAAACCTGC | ACAAACCAGT | CATCCTCACT | 420 |
| GGCGCCCAGG | TGCCAATCCG | TGTGCTGTGG | AATGACGCCC | GGGAAAACCT | GCTGGGGCG | 480 |
| TTGCTTGTGG | CCGGCCAATA | CATCATCCCT | GAGGTCTGCC | TGTTTATGAA | CAGTCAGCTG | 540 |
| TTTCGGGGAA | ACCGGGTAAC | CAAGGTGGAC | TCCCAGAAGT | TGAGGCCTT | CTGCTCCCCC | 600 |
| AATCTGTCCC | CACTAGCCAC | TGTGGGCGCG | GATGTCACAA | TTGCCTGGGA | CCTGGTGCGC | 660 |
| AAGGTCAACT | GGAAGGACCC | GCTGGTGGTG | CACAGCAACA | TGGAGCACGA | CGTGGCACTG | 720 |
| CTGCGCCTCT | ACCCTGGCAT | CCCGGCCTCC | CTGGTCCGGG | CATTCCTGCA | GCCCCCGCTC | 780 |
| AAGGGCGTGG | TCCTGGAGAC | CTTCGGCTCT | GGCAACGGGC | CGAGCAAGCC | CGACCTGCTG | 840 |

```
CAGGAGTTGC GGGCCGCGGC CCAGCGCGGC CTCATCATGG TCAACTGCAG CCAGTGCCTG     900

CGGGGGTCTG TGACCCCGGG CTATGCCACG AGCTTGGCGG GCGCCAACAT CGTGTCCGGC     960

TTAGACATGA CCTCAGAGGC CGCGCTGGCT AAGCTGTCCT ACGTGTTGGG CCTGCCGGAG    1020

CTGAGCCTGG AGCGCAGGCA GGAGCTGCTG GCCAAGGATC TTCGCGGGGA AATGACACTG    1080

CCCACGGCAG ACCTGCACCA GTCCTCTCCG CCGGGCAGCA CACTGGGCA AGGTGTCGCC     1140

CGGCTCTTTA GTCTGTTCGG TTGCCAGGAG GAAGATTCGG TGCAGGACGC CGTGATGCCC    1200

AGCCTGGCCC TGGCCTTGGC CCATGCTGGT GAACTCGAGG CTCTGCAGGC ACTTATGGAG    1260

CTGGGCAGTG ACCTGCGCCT AAAGGACTCT AATGGCCAAA CCCTGTTGCA TGTGGCTGCT    1320

CGGAATGGGC GTGATGGCGT GGTCACCATG CTGCTGCACA GAGGCATGGA TGTCAATGCC    1380

CGAGACCGAG ACGGCCTCAG CCCACTGCTG TTGGCTGTAC AGGGCAGGCA TCGGGAATGC    1440

ATCAGGCTGC TGCGGAAGGC TGGGGCCTGC CTGTCCCCCC AGGACCTGAA GGATGCAGGG    1500

ACCGAGCTGT GCAGGCTGGC ATCCAGGGCT GACATGGAAG GCCTGCAGGC ATGGGGCAG    1560

GCTGGGGCCG ACCTGCAGCA GCCGGGCTAT GATGGGCGCA GCGCTCTGTG TGTCGCAGAA    1620

GCAGCCGGGA ACCAGGAGGT GCTGGCCCTT CTGCGGAACC TGGCACTTGT AGGCCCGGAA    1680

GTGCCGCCTG CCATC                                                    1695
```

(2) INFORMATION FOR SEQ ID NO:4:

(i) SEQUENCE CHARACTERISTICS:
        (A) LENGTH: 1719 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

```
ATGGCGCGCG CGGTGGGGCC CGAGCGGAGG CTGCTGGCCG TCTACACCGG CGGCACCATT      60

GGCATGCGGA GTGAGCTCGG CGTGCTTGTG CCCGGGACGG GCCTGGCTGC CATCCTGAGG     120

ACACTGCCCA TGTTCCATGA CGAGGAGCAC GCCCGAGCCC GCGGCCTCTC TGAGGACACC     180

CTGGTGCTAC CCCCGGACAG CCGCAACCAG AGGATCCTCT ACACCGTGCT GGAGTGCCAG     240

CCCCTCTTCG ACTCCAGTGA CATGACCATC GCTGAGTGGG TTCGCGTTGC CCAGACCATC     300

AAGAGGCACT ACGAGCAGTA CCACGGCTTT GTGGTCATCC ACGGCACCGA CACCATGGCC     360

TTTGCTGCCT CGATGCTGTC CTTCATGCTG GAGAACCTGC AGAAGACTGT CATCCTCACT     420

GGGGCCCAGG TGCCCATCCA TGCCCTGTGG AGCGACGGCC GTGAGAACCT GCTGGGGGCA     480

CTGCTCATGG CTGGCCAGTA TGTGATCCCA GAGGTCTGCC TTTTCTTCCA GAATCAGCTG     540

TTTCGGGGCA ACCGGGCAAC CAAGGTAGAC GCTCGGAGGT TCGCAGCTTT CTGCTCCCCG     600

AACCTGCTGC CTCTGGCCAC AGTGGGTGCT GACATCACAA TCAACAGGGA GCTGGTGCGG     660

AAGGTGGACG GGAAGGCTGG GCTGGTGGTG CACAGCAGCA TGGAGCAGGA CGTGGGCCTG     720

CTGCGCCTCT ACCCTGGGAT CCCTGCCGCC CTGGTTCGGG CCTTCTTGCA GCCTCCCCTG     780

AAGGGCGTGG TCATGGAGAC CTTCGGTTCA GGGAACGGAC CCACCAAGCC CGACCTGCTG     840

CAGGAGCTGC GGGTGGCCAC CGAGCGCGGC CTGGTCATCG TCAACTGTAC CCACTGCCTC     900

CAGGGGGCTG TGACCACAGA CTATGCAGCT GGCATGGCCA TGGCGGGAGC CGGCGTCATC     960

TCAGGCTTCG ACATGACATC GGAGGCCGCC CTGGCCAAGC TATCGTATGT GCTGGGCCAG    1020

CCAGGGCTGA GCCTGGATGT CAGGAAGGAG CTGCTGACCA AGGACCTTCG GGGGGAGATG    1080
```

```
ACGCCACCCT CGGTGGAAGA GCGCCGGCCC TCACTGCAGG GCAACACGCT GGGCGGTGGG     1140

GTCTCCTGGC TCCTCAGTCT GAGCGGCAGC CAGGAGGCAG ATGCCCTGCG GAATGCCCTG     1200

GTGCCCAGCC TGGCCTGTGC TGCTGCCCAC GCCGGTGACG TGGAGGCGCT GCAGGCGCTT     1260

GTGGAGCTGG GCAGTGACCT GGGCCTGGTG GACTTTAACG GCCAAACCCC ACTGCACGCG     1320

GCCGCCCGGG GAGGCCACAC AGAGGCAGTC ACCATGCTGC TGCAGAGAGG TGTGGACGTG     1380

AACACCCGGG ACACGGATGG CTTCAGCCCG CTGCTGCTGG CCGTGCGGGG CAGGCATCCG     1440

GGTGTCATTG GGTTGCTGCG GGAAGCCGGG GCCTCCCTGT CCACCCAGGA GCTGGAGGAA     1500

GCAGGGACGG AGCTGTGCAG GCTGGCATAC AGGGCCGACC TCGAAGGCCT GCAGGTGTGG     1560

TGGCAGGCAG GGGCTGACCT GGGGCAGCCG GGCTATGACG GCACAGCGC CCTGCACGTC      1620

GCAGAGGCAG CCGGGAACCT GGCAGTGGTG GCCTTTCTAC AGAGCCTGGA GGGTGCGGTT     1680

GGTGCCCAGG CCCCATGCCC AGAAGTGCTG CCTGGTGTC                            1719
```

(2) INFORMATION FOR SEQ ID NO:5:

(i) SEQUENCE CHARACTERISTICS:
        (A) LENGTH: 324 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

```
ACCACTACTG AGTGGGTTCA GATTGCCCAA ACCATAGAGA GACACTACGC ACAGTACCAG      60

GGCTTTGTTG TCATCCATGG CACAGACACC ATGGCCTTTG CTGCCTCAGT GCTCTCTTCC     120

ATGCTGGAAA ACCTGCAGAA ACCAGTCGTC CTCACGGGTG CCCAGGTACC TATCCACGCA     180

CTGTGGAGTG ACGGCCGTGA GAACCTGCTG GGGGCTCTGC TCATGGCTGG CCAATACGTC     240

ATCCCTGAGG TCTGCCTGTT CTTCCAGAAT CAGCTTTTCC GGGGCAATCG GACAACCAAG     300

GTGGACGCTC GGAGGTTTGC CGCC                                            324
```

(2) INFORMATION FOR SEQ ID NO:6:

(i) SEQUENCE CHARACTERISTICS:
        (A) LENGTH: 565 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Ala Arg Ala Ser Gly Ser Glu Arg His Leu Leu Ile Tyr Thr
1               5                   10                  15

Gly Gly Thr Leu Gly Met Gln Ser Lys Gly Val Leu Val Pro Gly
                20                  25                  30

Pro Gly Leu Val Thr Leu Leu Arg Thr Leu Pro Met Phe His Asp Lys
                35                  40                  45

Glu Phe Ala Gln Ala Gln Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
                85                  90                  95
```

-continued

```
Ala Lys Ile Ile Glu Arg His Tyr Glu Gln Tyr Gln Gly Phe Val Val
            100                 105                 110

Ile His Gly Thr Asp Thr Met Ala Phe Gly Ala Ser Met Leu Ser Phe
        115                 120                 125

Met Leu Glu Asn Leu His Lys Pro Val Ile Leu Thr Gly Ala Gln Val
    130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Cys Ser Pro Asn Leu Ser Pro Leu Ala Thr Val
        195                 200                 205

Gly Ala Asp Val Thr Ile Ala Trp Asp Leu Val Arg Lys Val Asn Trp
    210                 215                 220

Lys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
                240                 245                 250

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Gln
        275                 280                 285

Arg Gly Leu Ile Met Val Asn Cys Ser Gln Cys Leu Arg Gly Ser Val
    290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Glu Arg Arg Gln Glu Leu Leu Ala Lys
            340                 345                 350

Asp Leu Arg Gly Glu Met Thr Leu Pro Thr Ala Asp Leu His Gln Ser
        355                 360                 365

Ser Pro Pro Gly Ser Thr Leu Gly Gln Gly Val Ala Arg Leu Phe Ser
    370                 375                 380

Leu Phe Gly Cys Gln Glu Glu Asp Ser Val Gln Asp Ala Val Met Pro
385                 390                 395                 400

Ser Leu Ala Leu Ala Leu Ala His Ala Gly Glu Leu Glu Ala Leu Gln
                405                 410                 415

Ala Leu Met Glu Leu Gly Ser Asp Leu Arg Leu Lys Asp Ser Asn Gly
            420                 425                 430

Gln Thr Leu Leu His Val Ala Ala Arg Asn Gly Arg Asp Gly Val Val
        435                 440                 445

Thr Met Leu Leu His Arg Gly Met Asp Val Asn Ala Arg Asp Arg Asp
    450                 455                 460

Gly Leu Ser Pro Leu Leu Leu Ala Val Gln Gly Arg His Arg Glu Cys
465                 470                 475                 480

Ile Arg Leu Leu Arg Lys Ala Gly Ala Cys Leu Ser Pro Gln Asp Leu
                485                 490                 495

Lys Asp Ala Gly Thr Glu Leu Cys Arg Leu Ala Ser Arg Ala Asp Met
            500                 505                 510

Glu Gly Leu Gln Ala Trp Gly Gln Ala Gly Ala Asp Leu Gln Gln Pro
```

```
            515                 520                 525
Gly Tyr Asp Gly Arg Ser Ala Leu Cys Val Ala Glu Ala Ala Gly Asn
            530                 535                 540

Gln Glu Val Leu Ala Leu Leu Arg Asn Leu Ala Leu Val Gly Pro Glu
545                 550                 555                 560

Val Pro Pro Ala Ile
                565
```

(2) INFORMATION FOR SEQ ID NO:7:

(i) SEQUENCE CHARACTERISTICS:
        (A) LENGTH: 573 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Met Ala Arg Ala Val Gly Pro Glu Arg Arg Leu Leu Ala Val Tyr Thr
1               5                   10                  15

Gly Gly Thr Ile Gly Met Arg Ser Glu Leu Gly Val Leu Val Pro Gly
                20                  25                  30

Thr Gly Leu Ala Ala Ile Leu Arg Thr Leu Pro Met Phe His Asp Glu
            35                  40                  45

Glu His Ala Arg Ala Arg Gly Leu Ser Glu Asp Thr Leu Val Leu Pro
        50                  55                  60

Pro Asp Ser Arg Asn Gln Arg Ile Leu Tyr Thr Val Leu Glu Cys Gln
65                  70                  75                  80

Pro Leu Phe Asp Ser Ser Asp Met Thr Ile Ala Glu Trp Val Arg Val
                85                  90                  95

Ala Gln Thr Ile Lys Arg His Tyr Glu Gln Tyr His Gly Phe Val Val
            100                 105                 110

Ile His Gly Thr Asp Thr Met Ala Phe Ala Ala Ser Met Leu Ser Phe
        115                 120                 125

Met Leu Glu Asn Leu Gln Lys Thr Val Ile Leu Thr Gly Ala Gln Val
130                 135                 140

Pro Ile His Ala Leu Trp Ser Asp Gly Arg Glu Asn Leu Leu Gly Ala
145                 150                 155                 160

Leu Leu Met Ala Gly Gln Tyr Val Ile Pro Glu Val Cys Leu Phe Phe
                165                 170                 175

Gln Asn Gln Leu Phe Arg Gly Asn Arg Ala Thr Lys Val Asp Ala Arg
            180                 185                 190

Arg Phe Ala Ala Phe Cys Ser Pro Asn Leu Pro Leu Ala Thr Val
        195                 200                 205

Gly Ala Asp Ile Thr Ile Asn Arg Glu Leu Val Arg Lys Val Asp Gly
210                 215                 220

Lys Ala Gly Leu Val Val His Ser Ser Met Glu Gln Asp Val Gly Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Met Glu Thr Phe Gly Ser Gly Asn
            260                 265                 270

Gly Pro Thr Lys Pro Asp Leu Leu Gln Glu Leu Arg Val Ala Thr Glu
        275                 280                 285

Arg Gly Leu Val Ile Val Asn Cys Thr His Cys Leu Gln Gly Ala Val
```

```
                290                 295                 300
Thr Thr Asp Tyr Ala Ala Gly Met Ala Met Ala Gly Ala Gly Val Ile
305                 310                 315                 320

Ser Gly Phe Asp Met Thr Ser Glu Ala Ala Leu Ala Lys Leu Ser Tyr
                325                 330                 335

Val Leu Gly Gln Pro Gly Leu Ser Leu Asp Val Arg Lys Glu Leu Leu
                340                 345                 350

Thr Lys Asp Leu Arg Gly Glu Met Thr Pro Pro Ser Val Glu Glu Arg
                355                 360                 365

Arg Pro Ser Leu Gln Gly Asn Thr Leu Gly Gly Val Ser Trp Leu
370                 375                 380

Leu Ser Leu Ser Gly Ser Gln Glu Ala Asp Ala Leu Arg Asn Ala Leu
385                 390                 395                 400

Val Pro Ser Leu Ala Cys Ala Ala His Ala Gly Asp Val Glu Ala
                405                 410                 415

Leu Gln Ala Leu Val Glu Leu Gly Ser Asp Leu Gly Leu Val Asp Phe
                420                 425                 430

Asn Gly Gln Thr Pro Leu His Ala Ala Arg Gly Gly His Thr Glu
                435                 440                 445

Ala Val Thr Met Leu Leu Gln Arg Gly Val Asp Val Asn Thr Arg Asp
450                 455                 460

Thr Asp Gly Phe Ser Pro Leu Leu Ala Val Arg Gly Arg His Pro
465                 470                 475                 480

Gly Val Ile Gly Leu Leu Arg Glu Ala Gly Ala Ser Leu Ser Thr Gln
                485                 490                 495

Glu Leu Glu Glu Ala Gly Thr Glu Leu Cys Arg Leu Ala Tyr Arg Ala
                500                 505                 510

Asp Leu Glu Gly Leu Gln Val Trp Trp Gln Ala Gly Ala Asp Leu Gly
                515                 520                 525

Gln Pro Gly Tyr Asp Gly His Ser Ala Leu His Val Ala Glu Ala Ala
                530                 535                 540

Gly Asn Leu Ala Val Val Ala Phe Leu Gln Ser Leu Glu Gly Ala Val
545                 550                 555                 560

Gly Ala Gln Ala Pro Cys Pro Glu Val Leu Pro Gly Val
                565                 570
```

(2) INFORMATION FOR SEQ ID NO:8:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Thr Thr Thr Glu Trp Val Gln Ile Ala Gln Thr Ile Glu Arg His Tyr
1               5                   10                  15

Ala Gln Tyr Gln Gly Phe Val Val Ile His Gly Thr Asp Thr Met Ala
                20                  25                  30

Phe Ala Ala Ser Val Leu Ser Ser Met Leu Glu Asn Leu Gln Lys Pro
                35                  40                  45

Val Val Leu Thr Gly Ala Gln Val Pro Ile His Ala Leu Trp Ser Asp
                50                  55                  60

Gly Arg Glu Asn Leu Leu Gly Ala Leu Leu Met Ala Gly Gln Tyr Val
```

```
65                  70                  75                  80
Ile Pro Glu Val Cys Leu Phe Phe Gln Asn Gln Leu Phe Arg Gly Asn
                    85                  90                  95

Arg Thr Thr Lys Val Asp Ala Arg Arg Phe Ala Ala
                100                 105
```

(2) INFORMATION FOR SEQ ID NO:9:

(i) SEQUENCE CHARACTERISTICS:
        (A) LENGTH: 1928 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 20..1714

(xi) SEQUENCE DESCRIPTION: SEQ ID NO:9:

```
GAGTGGCTTA GCCGCAGGC ATG GCG CGC GCA TCA GGC TCC GAG AGG CAC CTG      52
                    Met Ala Arg Ala Ser Gly Ser Glu Arg His Leu
                     1               5                  10

CTG CTC ATC TAC ACT GGC GGC ACT TTG GGC ATG CAG AGC AAG GGC GGG      100
Leu Leu Ile Tyr Thr Gly Gly Thr Leu Gly Met Gln Ser Lys Gly Gly
            15                  20                  25

GTG CTC GTC CCC GGC CCA GGC CTG GTC ACT CTG CTG CGG ACC CTG CCC      148
Val Leu Val Pro Gly Pro Gly Leu Val Thr Leu Leu Arg Thr Leu Pro
        30                  35                  40

ATG TTC CAT GAC AAG GAG TTC GCC CAG GCC CAG GGC CTC CCT GAC CAT      196
Met Phe His Asp Lys Glu Phe Ala Gln Ala Gln Gly Leu Pro Asp His
    45                  50                  55

GCT CTG GCG CTG CCC CCT GCC AGC CAC GGC CCC AGG GTC CTC TAC ACG      244
Ala Leu Ala Leu Pro Pro Ala Ser His Gly Pro Arg Val Leu Tyr Thr
60                  65                  70                  75

GTG CTG GAG TGC CAG CCC CTC TTG GAT TCC AGC GAC ATG ACC ATC GAT      292
Val Leu Glu Cys Gln Pro Leu Leu Asp Ser Ser Asp Met Thr Ile Asp
                80                  85                  90

GAT TGG ATT CGC ATA GCC AAG ATC ATA GAG AGG CAC TAT GAG CAG TAC      340
Asp Trp Ile Arg Ile Ala Lys Ile Ile Glu Arg His Tyr Glu Gln Tyr
            95                  100                 105

CAA GGC TTT GTG GTT ATC CAC GGC ACC GAC ACC ATG GCC TTT GGG GCC      388
Gln Gly Phe Val Val Ile His Gly Thr Asp Thr Met Ala Phe Gly Ala
        110                 115                 120

TCC ATG CTG TCC TTC ATG CTG GAA AAC CTG CAC AAA CCA GTC ATC CTC      436
Ser Met Leu Ser Phe Met Leu Glu Asn Leu His Lys Pro Val Ile Leu
    125                 130                 135

ACT GGC GCC CAG GTG CCA ATC CGT GTG CTG TGG AAT GAC GCC CGG GAA      484
Thr Gly Ala Gln Val Pro Ile Arg Val Leu Trp Asn Asp Ala Arg Glu
140                 145                 150                 155

AAC CTG CTG GGG GCG TTG CTT GTG GCC GGC CAA TAC ATC ATC CCT GAG      532
Asn Leu Leu Gly Ala Leu Leu Val Ala Gly Gln Tyr Ile Ile Pro Glu
                160                 165                 170

GTC TGC CTG TTT ATG AAC AGT CAG CTG TTT CGG GGA AAC CGG GTA ACC      580
Val Cys Leu Phe Met Asn Ser Gln Leu Phe Arg Gly Asn Arg Val Thr
            175                 180                 185

AAG GTG GAC TCC CAG AAG TTT GAG GCC TTC TGC TCC CCC AAT CTG TCC      628
Lys Val Asp Ser Gln Lys Phe Glu Ala Phe Cys Ser Pro Asn Leu Ser
        190                 195                 200

CCA CTA GCC ACT GTG GGC GCG GAT GTC ACA ATT GCC TGG GAC CTG GTG      676
Pro Leu Ala Thr Val Gly Ala Asp Val Thr Ile Ala Trp Asp Leu Val
```

-continued

```
              205                     210                     215
CGC AAG GTC AAC TGG AAG GAC CCG CTG GTG GTG CAC AGC AAC ATG GAG      724
Arg Lys Val Asn Trp Lys Asp Pro Leu Val Val His Ser Asn Met Glu
220                 225                 230                 235

CAC GAC GTG GCA CTG CTG CGC CTC TAC CCT GGC ATC CCG GCC TCC CTG      772
His Asp Val Ala Leu Leu Arg Leu Tyr Pro Gly Ile Pro Ala Ser Leu
                240                 245                 250

GTC CGG GCA TTC CTG CAG CCC CCG CTC AAG GGC GTG GTC CTG GAG ACC      820
Val Arg Ala Phe Leu Gln Pro Pro Leu Lys Gly Val Val Leu Glu Thr
            255                 260                 265

TTC GGC TCT GGC AAC GGG CCG AGC AAG CCC GAC CTG CTG CAG GAG TTG      868
Phe Gly Ser Gly Asn Gly Pro Ser Lys Pro Asp Leu Leu Gln Glu Leu
                270                 275                 280

CGG GCC GCG GCC CAG CGC GGC CTC ATC ATG GTC AAC TGC AGC CAG TGC      916
Arg Ala Ala Ala Gln Arg Gly Leu Ile Met Val Asn Cys Ser Gln Cys
            285                 290                 295

CTG CGG GGG TCT GTG ACC CCG GGC TAT GCC ACG AGC TTG GCG GGC GCC      964
Leu Arg Gly Ser Val Thr Pro Gly Tyr Ala Thr Ser Leu Ala Gly Ala
300                 305                 310                 315

AAC ATC GTG TCC GGC TTA GAC ATG ACC TCA GAG GCC GCG CTG GCT AAG     1012
Asn Ile Val Ser Gly Leu Asp Met Thr Ser Glu Ala Ala Leu Ala Lys
                320                 325                 330

CTG TCC TAC GTG TTG GGC CTG CCG GAG CTG AGC CTG GAG CGC AGG CAG     1060
Leu Ser Tyr Val Leu Gly Leu Pro Glu Leu Ser Leu Glu Arg Arg Gln
            335                 340                 345

GAG CTG CTG GCC AAG GAT CTT CGC GGG GAA ATG ACA CTG CCC ACG GCA     1108
Glu Leu Leu Ala Lys Asp Leu Arg Gly Glu Met Thr Leu Pro Thr Ala
                350                 355                 360

GAC CTG CAC CAG TCC TCT CCG CCG GGC AGC ACA CTG GGG CAA GGT GTC     1156
Asp Leu His Gln Ser Ser Pro Pro Gly Ser Thr Leu Gly Gln Gly Val
365                 370                 375

GCC CGG CTC TTT AGT CTG TTC GGT TGC CAG GAG GAA GAT TCG GTG CAG     1204
Ala Arg Leu Phe Ser Leu Phe Gly Cys Gln Glu Glu Asp Ser Val Gln
            385                 390                 395

GAC GCC GTG ATG CCC AGC CTG GCC CTG GCC TTG GCC CAT GCT GGT GAA     1252
Asp Ala Val Met Pro Ser Leu Ala Leu Ala Leu Ala His Ala Gly Glu
                400                 405                 410

CTC GAG GCT CTG CAG GCA CTT ATG GAG CTG GGC AGT GAC CTG CGC CTA     1300
Leu Glu Ala Leu Gln Ala Leu Met Glu Leu Gly Ser Asp Leu Arg Leu
            415                 420                 425

AAG GAC TCT AAT GGC CAA ACC CTG TTG CAT GTG GCT GCT CGG AAT GGG     1348
Lys Asp Ser Asn Gly Gln Thr Leu Leu His Val Ala Ala Arg Asn Gly
                430                 435                 440

CGT GAT GGC GTG GTC ACC ATG CTG CTG CAC AGA GGC ATG GAT GTC AAT     1396
Arg Asp Gly Val Val Thr Met Leu Leu His Arg Gly Met Asp Val Asn
            445                 450                 455

GCC CGA GAC CGA GAC GGC CTC AGC CCA CTG CTG TTG GCT GTA CAG GGC     1444
Ala Arg Asp Arg Asp Gly Leu Ser Pro Leu Leu Leu Ala Val Gln Gly
460                 465                 470                 475

AGG CAT CGG GAA TGC ATC AGG CTG CTG CGG AAG GCT GGG GCC TGC CTG     1492
Arg His Arg Glu Cys Ile Arg Leu Leu Arg Lys Ala Gly Ala Cys Leu
                480                 485                 490

TCC CCC CAG GAC CTG AAG GAT GCA GGG ACC GAG CTG TGC AGG CTG GCA     1540
Ser Pro Gln Asp Leu Lys Asp Ala Gly Thr Glu Leu Cys Arg Leu Ala
            495                 500                 505

TCC AGG GCT GAC ATG GAA GGC CTG CAG GCA TGG GGG CAG GCT GGG GCC     1588
Ser Arg Ala Asp Met Glu Gly Leu Gln Ala Trp Gly Gln Ala Gly Ala
                510                 515                 520

GAC CTG CAG CAG CCG GGC TAT GAT GGG CGC AGC GCT CTG TGT GTC GCA     1636
```

```
Asp Leu Gln Gln Pro Gly Tyr Asp Gly Arg Ser Ala Leu Cys Val Ala
    525                 530                 535

GAA GCA GCC GGG AAC CAG GAG GTG CTG GCC CTT CTG CGG AAC CTG GCA      1684
Glu Ala Ala Gly Asn Gln Glu Val Leu Ala Leu Leu Arg Asn Leu Ala
540                 545                 550                 555

CTT GTA GGC CCG GAA GTG CCG CCT GCC ATC TGATCGCCAG CAATCCCGCT        1734
Leu Val Gly Pro Glu Val Pro Pro Ala Ile
                560                 565

GTGGTGTGAG CCACTCCGCC ATCTGCTGCT TTGACCCACT CGAGGGACCC TAGCACACGA    1794

CCCCCCAGCA GGATGCACCC CACTACTTAG AGTATACCCC AGGCTGGCTC AGTGACAAGC    1854

TGCAAAGGTC TTTGTTGGCA GAACAGCAAT AAAGTAACTA CAGAGTGGCC AAAAAAAAAA    1914

AAAAAAAAAA AAAA                                                      1928

(2) INFORMATION FOR SEQ ID NO:10:

(i) SEQUENCE CHARACTERISTICS:
        (A) LENGTH: 2096 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 20..1714

(xi) SEQUENCE DESCRIPTION: SEQ ID NO:10:

CGCCCCGGGC CTCCTCCGCG CAGTCCCTGA GTCCCGCAGG CCCTGCGTCC CCGCTGCACA      60

CCCCCGTCCA CTCCCGTGGT CCCCGGTCCG GC ATG GCG CGC GCG GTG GGG CCC      113
                                   Met Ala Arg Ala Val Gly Pro
                                     1               5

GAG CGG AGG CTG CTG GCC GTC TAC ACC GGC GGC ACC ATT GGC ATG CGG       161
Glu Arg Arg Leu Leu Ala Val Tyr Thr Gly Gly Thr Ile Gly Met Arg
         10                  15                  20

AGT GAG CTC GGC GTG CTT GTG CCC GGG ACG GGC CTG GCT GCC ATC CTG       209
Ser Glu Leu Gly Val Leu Val Pro Gly Thr Gly Leu Ala Ala Ile Leu
 25                  30                  35

AGG ACA CTG CCC ATG TTC CAT GAC GAG GAG CAC GCC CGA GCC CGC GGC       257
Arg Thr Leu Pro Met Phe His Asp Glu Glu His Ala Arg Ala Arg Gly
40                  45                  50                  55

CTC TCT GAG GAC ACC CTG GTG CTA CCC CCG GAC AGC CGC AAC CAG AGG       305
Leu Ser Glu Asp Thr Leu Val Leu Pro Pro Asp Ser Arg Asn Gln Arg
                 60                  65                  70

ATC CTC TAC ACC GTG CTG GAG TGC CAG CCC CTC TTC GAC TCC AGT GAC       353
Ile Leu Tyr Thr Val Leu Glu Cys Gln Pro Leu Phe Asp Ser Ser Asp
             75                  80                  85

ATG ACC ATC GCT GAG TGG GTT CGC GTT GCC CAG ACC ATC AAG AGG CAC       401
Met Thr Ile Ala Glu Trp Val Arg Val Ala Gln Thr Ile Lys Arg His
         90                  95                 100

TAC GAG CAG TAC CAC GGC TTT GTG GTC ATC CAC GGC ACC GAC ACC ATG       449
Tyr Glu Gln Tyr His Gly Phe Val Val Ile His Gly Thr Asp Thr Met
    105                 110                 115

GCC TTT GCT GCC TCG ATG CTG TCC TTC ATG CTG GAG AAC CTG CAG AAG       497
Ala Phe Ala Ala Ser Met Leu Ser Phe Met Leu Glu Asn Leu Gln Lys
120                 125                 130                 135

ACT GTC ATC CTC ACT GGG GCC CAG GTG CCC ATC CAT GCC CTG TGG AGC       545
Thr Val Ile Leu Thr Gly Ala Gln Val Pro Ile His Ala Leu Trp Ser
                140                 145                 150

GAC GGC CGT GAG AAC CTG CTG GGG GCA CTG CTC ATG GCT GGC CAG TAT       593
Asp Gly Arg Glu Asn Leu Leu Gly Ala Leu Leu Met Ala Gly Gln Tyr
```

-continued

```
Asp Gly Arg Glu Asn Leu Leu Gly Ala Leu Leu Met Ala Gly Gln Tyr
            155                 160                 165

GTG ATC CCA GAG GTC TGC CTT TTC TTC CAG AAT CAG CTG TTT CGG GGC        641
Val Ile Pro Glu Val Cys Leu Phe Phe Gln Asn Gln Leu Phe Arg Gly
            170                 175                 180

AAC CGG GCA ACC AAG GTA GAC GCT CGG AGG TTC GCA GCT TTC TGC TCC        689
Asn Arg Ala Thr Lys Val Asp Ala Arg Arg Phe Ala Ala Phe Cys Ser
        185                 190                 195

CCG AAC CTG CTG CCT CTG GCC ACA GTG GGT GCT GAC ATC ACA ATC AAC        737
Pro Asn Leu Leu Pro Leu Ala Thr Val Gly Ala Asp Ile Thr Ile Asn
200                 205                 210                 215

AGG GAG CTG GTG CGG AAG GTG GAC GGG AAG GCT GGG CTG GTG GTG CAC        785
Arg Glu Leu Val Arg Lys Val Asp Gly Lys Ala Gly Leu Val Val His
                220                 225                 230

AGC AGC ATG GAG CAG GAC GTG GGC CTG CTG CGC CTC TAC CCT GGG ATC        833
Ser Ser Met Glu Gln Asp Val Gly Leu Leu Arg Leu Tyr Pro Gly Ile
            235                 240                 245

CCT GCC GCC CTG GTT CGG GCC TTC TTG CAG CCT CCC CTG AAG GGC GTG        881
Pro Ala Ala Leu Val Arg Ala Phe Leu Gln Pro Pro Leu Lys Gly Val
            250                 255                 260

GTC ATG GAG ACC TTC GGT TCA GGG AAC GGA CCC ACC AAG CCC GAC CTG        929
Val Met Glu Thr Phe Gly Ser Gly Asn Gly Pro Thr Lys Pro Asp Leu
            265                 270                 275

CTG CAG GAG CTG CGG GTG GCC ACC GAG CGC GGC CTG GTC ATC GTC AAC        977
Leu Gln Glu Leu Arg Val Ala Thr Glu Arg Gly Leu Val Ile Val Asn
280                 285                 290                 295

TGT ACC CAC TGC CTC CAG GGG GCT GTG ACC ACA GAC TAT GCA GCT GGC       1025
Cys Thr His Cys Leu Gln Gly Ala Val Thr Thr Asp Tyr Ala Ala Gly
                300                 305                 310

ATG GCC ATG GCG GGA GCC GGC GTC ATC TCA GGC TTC GAC ATG ACA TCG       1073
Met Ala Met Ala Gly Ala Gly Val Ile Ser Gly Phe Asp Met Thr Ser
            315                 320                 325

GAG GCC GCC CTG GCC AAG CTA TCG TAT GTG CTG GGC CAG CCA GGG CTG       1121
Glu Ala Ala Leu Ala Lys Leu Ser Tyr Val Leu Gly Gln Pro Gly Leu
            330                 335                 340

AGC CTG GAT GTC AGG AAG GAG CTG CTG ACC AAG GAC CTT CGG GGG GAG       1169
Ser Leu Asp Val Arg Lys Glu Leu Leu Thr Lys Asp Leu Arg Gly Glu
            345                 350                 355

ATG ACG CCA CCC TCG GTG GAA GAG CGC CGG CCC TCA CTG CAG GGC AAC       1217
Met Thr Pro Pro Ser Val Glu Glu Arg Arg Pro Ser Leu Gln Gly Asn
360                 365                 370                 375

ACG CTG GGC GGT GGG GTC TCC TGG CTC CTC AGT CTG AGC GGC AGC CAG       1265
Thr Leu Gly Gly Gly Val Ser Trp Leu Leu Ser Leu Ser Gly Ser Gln
                380                 385                 390

GAG GCA GAT GCC CTG CGG AAT GCC CTG GTG CCC AGC CTG GCC TGT GCT       1313
Glu Ala Asp Ala Leu Arg Asn Ala Leu Val Pro Ser Leu Ala Cys Ala
            395                 400                 405

GCT GCC CAC GCC GGT GAC GTG GAG GCG CTG CAG GCG CTT GTG GAG CTG       1361
Ala Ala His Ala Gly Asp Val Glu Ala Leu Gln Ala Leu Val Glu Leu
            410                 415                 420

GGC AGT GAC CTG GGC CTG GTG GAC TTT AAC GGC CAA ACC CCA CTG CAC       1409
Gly Ser Asp Leu Gly Leu Val Asp Phe Asn Gly Gln Thr Pro Leu His
            425                 430                 435

GCG GCC GCC CGG GGA GGC CAC ACA GAG GCA GTC ACC ATG CTG CTG CAG       1457
Ala Ala Ala Arg Gly Gly His Thr Glu Ala Val Thr Met Leu Leu Gln
440                 445                 450                 455

AGA GGT GTG GAC GTG AAC ACC CGG GAC ACG GAT GGC TTC AGC CCG CTG       1505
Arg Gly Val Asp Val Asn Thr Arg Asp Thr Asp Gly Phe Ser Pro Leu
                460                 465                 470
```

```
CTG CTG GCC GTG CGG GGC AGG CAT CCG GGT GTC ATT GGG TTG CTG CGG        1553
Leu Leu Ala Val Arg Gly Arg His Pro Gly Val Ile Gly Leu Leu Arg
            475                 480                 485

GAA GCC GGG GCC TCC CTG TCC ACC CAG GAG CTG GAG GAA GCA GGG ACG        1601
Glu Ala Gly Ala Ser Leu Ser Thr Gln Glu Leu Glu Glu Ala Gly Thr
            490                 495                 500

GAG CTG TGC AGG CTG GCA TAC AGG GCC GAC CTC GAA GGC CTG CAG GTG        1649
Glu Leu Cys Arg Leu Ala Tyr Arg Ala Asp Leu Glu Gly Leu Gln Val
            505                 510                 515

TGG TGG CAG GCA GGG GCT GAC CTG GGG CAG CCG GGC TAT GAC GGG CAC        1697
Trp Trp Gln Ala Gly Ala Asp Leu Gly Gln Pro Gly Tyr Asp Gly His
520                 525                 530                 535

AGC GCC CTG CAC GTC GCA GAG GCA GCC GGG AAC CTG GCA GTG GTG GCC        1745
Ser Ala Leu His Val Ala Glu Ala Ala Gly Asn Leu Ala Val Val Ala
            540                 545                 550

TTT CTA CAG AGC CTG GAG GGT GCG GTT GGT GCC CAG GCC CCA TGC CCA        1793
Phe Leu Gln Ser Leu Glu Gly Ala Val Gly Ala Gln Ala Pro Cys Pro
            555                 560                 565

GAA GTG CTG CCT GGT GTC TAACCTGAAG GCGTCCTGCT GCAGTATAAG              1841
Glu Val Leu Pro Gly Val
            570

CCATTCCTTC CTCCCATGAC CTGCTGGAGG GGTCTCAGGC ATGACCCCAC TGCTGGGGCT     1901

GCTTCCCAGC CTGCTCTCAT GTAAAGCCTG AAGGCCTTTG TTGGGCAGGA CGGCAATAAA     1961

GTCTCTGACA TCCCCTCACC AGGTCTGTAC AGCCTGGCTC TGAGAGGCTC TGTCTGGGTC     2021

CGGGACTGTG AAAAAAAAAA AAAAAAAAAA AAAAAAAAAA AAAAAAAAAA AAAAAAAAAA     2081

AAAAAAAAAA AAAAA                                                     2096

(2) INFORMATION FOR SEQ ID NO:11:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Leu Tyr Pro Gly Ile Pro Ala Ser Leu Val Arg
1               5                   10

(2) INFORMATION FOR SEQ ID NO:12:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

His Leu Leu Leu Ile Tyr Thr Gly Gly Thr Leu Gly Met Gln Ser Lys
1               5                   10                  15

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO:13:

Ser Phe Met Leu Glu Asn Leu His Lys
1               5

(2) INFORMATION FOR SEQ ID NO:14:

(i) SEQUENCE CHARACTERISTICS:
            (A) LENGTH: 324 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:14:

| ACC ACT ACT GAG TGG GTT CAG ATT GCC CAA ACC ATA GAG AGA CAC TAC | 48 |
|---|---|
| Thr Thr Thr Glu Trp Val Gln Ile Ala Gln Thr Ile Glu Arg His Tyr | |
| 1           5                   10                  15 | |

| GCA CAG TAC CAG GGC TTT GTT GTC ATC CAT GGC ACA GAC ACC ATG GCC | 96 |
|---|---|
| Ala Gln Tyr Gln Gly Phe Val Val Ile His Gly Thr Asp Thr Met Ala | |
|           20                  25                  30 | |

| TTT GCT GCC TCA GTG CTC TCT TCC ATG CTG GAA AAC CTG CAG AAA CCA | 144 |
|---|---|
| Phe Ala Ala Ser Val Leu Ser Ser Met Leu Glu Asn Leu Gln Lys Pro | |
|       35                  40                  45 | |

| GTC GTC CTC ACG GGT GCC CAG GTA CCT ATC CAC GCA CTG TGG AGT GAC | 192 |
|---|---|
| Val Val Leu Thr Gly Ala Gln Val Pro Ile His Ala Leu Trp Ser Asp | |
| 50                  55                  60 | |

| GGC CGT GAG AAC CTG CTG GGG GCT CTG CTC ATG GCT GGC CAA TAC GTC | 240 |
|---|---|
| Gly Arg Glu Asn Leu Leu Gly Ala Leu Leu Met Ala Gly Gln Tyr Val | |
| 65                  70                  75                  80 | |

| ATC CCT GAG GTC TGC CTG TTC TTC CAG AAT CAG CTT TTC CGG GGC AAT | 288 |
|---|---|
| Ile Pro Glu Val Cys Leu Phe Phe Gln Asn Gln Leu Phe Arg Gly Asn | |
|           85                  90                  95 | |

| CGG ACA ACC AAG GTG GAC GCT CGG AGG TTT GCC GCC | 324 |
|---|---|
| Arg Thr Thr Lys Val Asp Ala Arg Arg Phe Ala Ala | |
|           100                 105 | |

(2) INFORMATION FOR SEQ ID NO:15:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:15:

GGNATGCARW SNAAR                                                   15

(2) INFORMATION FOR SEQ ID NO:16:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:16:

GCNGGDATNC CNGGRTA                                                 17

(2) INFORMATION FOR SEQ ID NO:17:

(i) SEQUENCE CHARACTERISTICS:
            (A) LENGTH: 17 base pairs

-continued

```
        (B) TYPE: nucleic acid
        (C) STRANDEDNESS: single
        (D) TOPOLOGY: linear (xi) SEQUENCE DESCRIPTION: SEQ ID NO:17:

TTYATGYTNG ARAAYYT                                                          17

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:18:

TTCGACTCCA GTGACATG                                                         18

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:19:

CAGGTTCGGG GAGCAGAA                                                         18
```